(12) United States Patent
Ekinci et al.

(10) Patent No.: US 10,604,784 B2
(45) Date of Patent: Mar. 31, 2020

(54) METHOD AND DEVICE FOR ANTIBIOTIC SUSCEPTIBILITY TESTING BASED ON FLUCTUATIONS OF ELECTRICAL RESISTANCE IN A MICROCHANNEL

(71) Applicant: TRUSTEES OF BOSTON UNIVERSITY, Boston, MA (US)

(72) Inventors: Kamil Ekinci, Cambridge, MA (US); Le Li, Boston, MA (US); Chuanhua Duan, Newton, MA (US); Vural Kara, Allston, MA (US); Deborah Stearns-Kurosawa, Waban, MA (US)

(73) Assignee: Trustees of Boston University, Boston, MA (US)

( * ) Notice: Subject to any disclaimer, the term of this patent is extended or adjusted under 35 U.S.C. 154(b) by 99 days.

(21) Appl. No.: 15/669,069

(22) Filed: Aug. 4, 2017

(65) Prior Publication Data
US 2018/0051311 A1    Feb. 22, 2018

Related U.S. Application Data

(60) Provisional application No. 62/371,417, filed on Aug. 5, 2016.

(51) Int. Cl.
*C12Q 1/04* (2006.01)
*C12Q 1/18* (2006.01)
(Continued)

(52) U.S. Cl.
CPC ............. *C12Q 1/18* (2013.01); *G01N 27/021* (2013.01); *G01N 33/48735* (2013.01); *B01L 3/502761* (2013.01)

(58) Field of Classification Search
CPC ...................................................... C12Q 1/04
See application file for complete search history.

(56) References Cited

U.S. PATENT DOCUMENTS 2,656,508 A    10/1953  Coulter
2002/0140414 A1    10/2002  Sohn et al.
(Continued)

OTHER PUBLICATIONS

Amphasys AG, "Amphasys—Impedance Microflow Cytometry—The Technology".
(Continued)

*Primary Examiner* — Rosanne Kosson
(74) *Attorney, Agent, or Firm* — Nixon Peabody LLP

(57) ABSTRACT

A system and method for antibiotic susceptibility testing efficiently determines whether bacteria are alive or have been killed by antibiotic treatment. The antibiotic susceptibility testing device includes at least one reservoir into which a bacteria solution is introduced and a microfluidic channel connected to the reservoir, wherein the cross-sectional size of the microfluidic channel is selected to be comparable to the size of the bacterium to be tested. Furthermore, the electrical resistance or voltage signal across the microchannel is monitored as bacteria swim into and out of the channel. Alternatively, a small population of bacteria can be immobilized in the microchannel. The resistance or voltage signal fluctuates when the bacteria are alive and moving in and out of the channel or wiggling on the microchannel walls. If the bacteria are dead, they have limited motility and the signal fluctuations are significantly smaller. By monitoring the signal fluctuations, the antibiotic susceptibility testing device can determine whether or not bacteria are alive, thus enabling antibiotic susceptibility testing of bacteria.

6 Claims, 27 Drawing Sheets
(6 of 27 Drawing Sheet(s) Filed in Color)

(51) Int. Cl.
*G01N 27/02* (2006.01)
*G01N 33/487* (2006.01)
*B01L 3/00* (2006.01)

(56) References Cited

U.S. PATENT DOCUMENTS

| | | | |
|---|---|---|---|
| 2005/0059105 A1* | 3/2005 | Alocilja | G01N 33/5438 |
| | | | 435/7.32 |
| 2005/0118705 A1 | 6/2005 | Rabbitt et al. | |
| 2005/0211559 A1 | 9/2005 | Kayyem | |
| 2014/0091012 A1 | 4/2014 | Ros et al. | |
| 2014/0128285 A1 | 5/2014 | Rowat et al. | |
| 2016/0010138 A1 | 1/2016 | Shamsheyeva et al. | |
| 2016/0161392 A1 | 6/2016 | Ionescu-Zanetti et al. | |

OTHER PUBLICATIONS

Bueno, "Biosensors in Antimicrobial Drug Discovery: Since Biology until Screening Platforms", Microbial & Biochemical Technology S10 (2014). (10 pages).

Chauhan et al., "Comparative efficacy of antibiotic sensitivity tests for management of acute clinical *Escherichia coli* mastitis in crossbred cow", Journal of Livestock Science 7:41-45 (2016).

Chen et al., "Antimicrobial Susceptibility Testing Using High Surface-to-Volume Ratio Microchannels", Analytical Chemistry 82:1012-1019 (2010).

Chen et al., "Microfluidic Impedance Flow Cytometry Enabling High-Throughput Single-Cell Electrical Property Characterization", International Journal of Molecular Sciences 16:9804-9830 (2015).

Huang et al., "Direct Antimicrobial Susceptibility Testing of Gram-Negative Bacilli in Blood Cultures by an Electrochemical Method", Journal of Clinical Microbiology 36(10):2882-2886 (1998).

Jagtiani et al., "High Throughput Microfluidic Electrical Impedance Flow Cytometry for Assay of Micro Particles", Micro and Nanosystems 2(4):1-11 (2010).

Kim et al., "An optical microfluidic platform for spatiotemporal biofilm treatment monitoring", Journal of Micromechanics and Microengineering 26:015013 (2016). (12 pages).

Lissandrello et al., "Nanomechanical motion of *Escherichia coli* adhered to a surface", Applied Physics Letters 105:113701 (2014). (6 pages).

Liu et al., "Rapid Antimicrobial Susceptibility Testing with Electrokinetics Enhanced Biosensors for Diagnosis of Acute Bacterial Infections", Annals of Biomedical Engineering 42(11): 2314-2321 (2014).

Liu et al., "Rapid bacterial antibiotic susceptibility test based on simple surface-enhanced Raman spectroscopic biomarkers", Scientific Reports 6:23375 (2016). (15 pages).

Lu et al., "Single Cell Antimicrobial Susceptibility Testing by Confined Microchannels and Electrokinetic Loading", Analytical Chemistry 85:3971-3976 (2013).

Price et al., "Rapid antibiotic susceptibility phenotypic characterization of *Staphylococcus aureus* using automated microscopy of small numbers of cells", Journal of Microbiological Methods 98:50-58 (2014).

Ruegg et al., "Milk Quality and Mastitis Tests", University of Wisconsin, Madison 1-33 (2002).

Van Belkum et al., "Next-Generation Antimicrobial Susceptibility Testing", Journal of Clinical Microbiology 51(7): 2018-2024 (2013).

Li et al., "Nanoporous membranes for microfluidic concentration prior to electrophoretic separation of proteins in urine", Analytical Chemistry (2016). (29 pages).

Sun et al., "Single-cell microfluidic impedance cytometry: a review", Microfluidics and Nanofluidics 8:423-443 (2010).

* cited by examiner

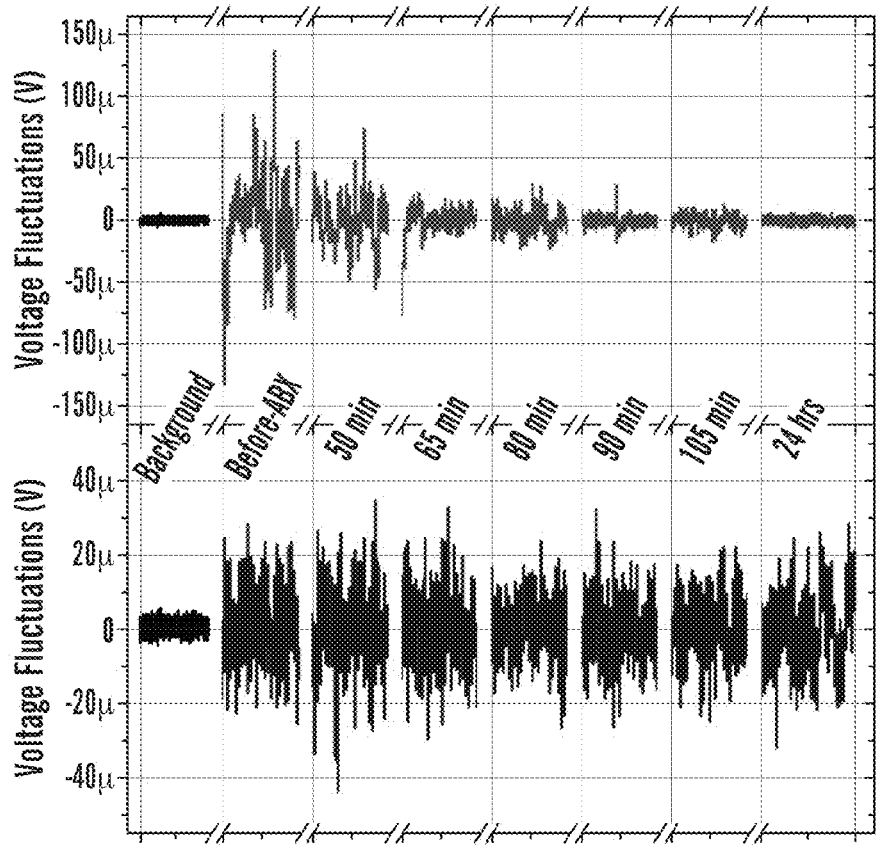
FIG. 13A
FIG. 13B
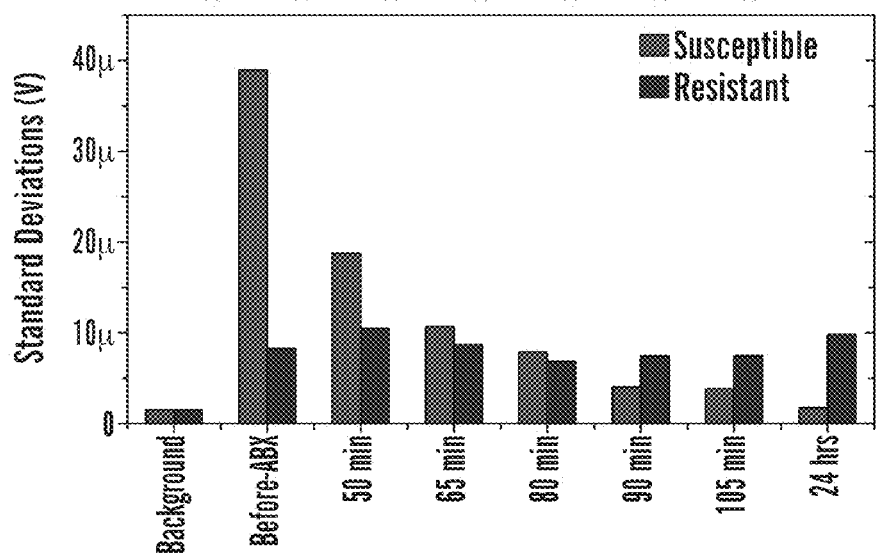
FIG. 13C

METHOD AND DEVICE FOR ANTIBIOTIC SUSCEPTIBILITY TESTING BASED ON FLUCTUATIONS OF ELECTRICAL RESISTANCE IN A MICROCHANNEL

CROSS-REFERENCE TO RELATED APPLICATIONS

This application claims any and all benefits as provided by law including benefit under 35 U.S.C. § 119(e) of the U.S. Provisional Application No. 62/371,417, filed Aug. 5, 2016, the contents of which are incorporated herein by reference in its entirety.

STATEMENT REGARDING FEDERALLY SPONSORED RESEARCH

Not Applicable.

TECHNICAL FIELD

The present invention relates to an antibiotic susceptibility testing apparatus for determining whether or not bacteria are live, and more particularly antibiotic susceptibility testing of bacteria.

BACKGROUND

Multi-drug resistant bacteria affect 2 million people in the U.S. every year, resulting in 23,000 deaths and causing an economic burden of an estimated $20 billion. The problem is exacerbated by the fact that development of new antibacterial agents has slowed down in the past decade. In short, bacteria are gaining resistance to available antibiotics at a rate faster than new antibiotics can be developed and brought to market.

In order to impede the takeover by resistant strains and to preserve the existing antibiotics, physicians must improve the process of prescribing antibiotics. Ideally, an antibiotic therapy should start only after confirming the susceptibility of the infecting bacteria to the antibiotic. However, physicians typically treat serious infections empirically by prescribing broad-spectrum antibiotics, because standard antibiotic susceptibility tests (ASTs) require long cell culturing steps. An antibiotic susceptibility test (AST) determines whether or not bacterial isolates from a patient's blood, wound specimens, or urine are susceptible to administered antibiotics. One of the gold standard tests, a broth dilution test, is performed by preparing a set of bacteria solutions, which are incubated overnight in the presence of different antibiotics with different concentrations. If the bacteria are resistant to the antibiotic, they multiply and the solution eventually becomes turbid. The limits of a typical optical measurement require the bacteria solution to be incubated for 16-20 hours. Similarly, the disk diffusion method is performed by applying a bacterial inoculum to the surface of an agar plate, on which antibiotic disks are placed. After incubation for 16-24 hours, the antibiotic inhibits the bacteria growth in the regions where it diffuses. The susceptibility of the bacterial strain can be determined from the size of the bacteria-free zones around the antibiotic disks.

However, both these tests have a shared shortcoming: one has to wait long enough such that the population reaches minimum detectable growth levels. Accordingly, there exists in the art a need for novel, rapid, sensitive and robust methods to determine the antibiotic susceptibility of bacteria.

It is clear that the above-described mainstay methods have limitations, and multi-drug resistant bacteria pose a grand challenge in global healthcare. Hence, the development of rapid antibiotic susceptibility tests (ASTs) is an active research area, with many publications and patents. The focus is on observing bacterial resistance at early stages of cell growth. Polymerase chain reaction (PCR) is the quintessential genotypic method. PCR directly detects the resistance gene of a very small bacterial sample and can provide fast identification of antibiotic resistance. However, it has limited utility, because only a few resistance genes are firmly associated with phenotypic antibiotic resistance. There are simply too many genetic mutations, acquisitions, and expressions to be routinely identified by current PCR techniques. Further, the use of PCR at point-of-care settings remains challenging.

Phenotypic methods, on the other hand, are based on observable characteristics of bacteria. Novel phenotypic ASTs typically employ microfluidics and microdevices, because these devices allow for effective use of samples and multiplexing. Researchers have been exploring different approaches based on microfluidics. In the first type of experiments, the growth of bacteria was directly observed in small volumes (e.g., microfluidic channels) in order to determine susceptibility to different antibiotics. This approach was pushed down to the single cell limit by confining cells in drug-infused nano and pico-liter droplets. In another approach, bacteria were adhered to oscillating microstructures, such as microcantilevers or magnetic microbeads, under administered antibiotics; here, the oscillation frequency decreased due to added bacteria mass if the bacteria multiplied, indicating resistance. Finally, measuring the physical or chemical properties of a medium (e.g., changes in electrical impedance or pH) due to bacterial proliferation allowed for measuring microbial growth. The changes with administered antibiotics then provided the desired susceptibility testing.

While most of the above-mentioned techniques are ingenious, very few have found their ways into the mainstream. There are still several major challenges. Some techniques require delicate microscopy or are too complicated to be implemented at point-of-care settings. Others rely upon labeling (e.g., fluorescent labeling), which limits utility. If the test determines susceptibility based on whether or not the bacteria are growing, the heterogeneity of the antimicrobial response of bacteria becomes an issue. In summary, there is a significant need for new approaches.

SUMMARY

The present invention is directed to methods and system for antibiotic susceptibility testing. Specifically, the antibiotic susceptibility testing system according to the invention includes at least one reservoir into which a bacteria solution can be introduced. The testing system includes a microfluidic channel connected to the reservoir and the bacteria in the solution are free to swim into the microfluidic channel. The resistance or conductivity of electric currents through the channel can be monitored as the bacteria swim into and out of the microfluidic channel. The movement of the live bacteria into and out of microfluidic channel can be detected as fluctuations in the measured resistance or conductivity. A related approach is based on capturing/immobilizing a small population of bacteria (~50 cells) inside the tiny microfluidic channel and the nanomechanical fluctuations of surface-adhered bacteria can be measured as fluctuations in the measured resistance or conductivity. A signal measuring device can be used to measure changes in the current or voltage through the microchannel over time. For example, the signal measuring device can include an oscilloscope, a digital signal processor, an analog signal processor, an ammeter, a capacitance meter, a multimeter, a computer, a programmable controller, etc.

The measured signal fluctuations in the resistance (or conductivity) caused by live bacteria can be distinguished from signals produced by dead bacteria in solution because dead bacteria have limited motility and the baseline fluctuations in the signal are significantly smaller (e.g., caused by thermal and Brownian motion) than the signal fluctuations when live bacteria are present. Accordingly, a method and system for testing antibiotic susceptibility is provided whereby a bacterial solution can be introduced into the system and a baseline of resistance (or conductivity) can be determined and used to evaluate any change in resistance (or conductivity) after the introduction of antibiotics into the reservoir to determine susceptibility. The system can determine the Root Mean Square (RMS) resistance, current or voltage of the signal fluctuations and compare the RMS signal value obtained from the microchannel when the bacteria are in the microchannel to the baseline RMS signal value obtained before the bacteria enter the microchannel to determine the presence of live bacteria in the microchannel.

This differs from Coulter counters, flow cytometers and other similar devices, wherein particles or cells are pushed through a constriction, either by a flow or by an electric field, and counted (i.e., detected) one by one.

The present invention provides a new paradigm of detection. The activity of live bacteria can be detected, monitored and characterized, for example, for determining the viability of the bacteria. The activity of dead bacteria can be distinguished because the signal fluctuations are significantly reduced—dead bacteria move only due to Brownian and thermal motion, which is smaller by orders of magnitude.

One aspect of the technology described herein relates to an antibiotic susceptibility testing system adapted to include a reservoir directly connected to a microchannel and bacteria from the reservoir are free to move into the microchannel. The microchannel can further include a second, antibiotic reservoir directly connected to the microchannel by pores that are large enough to pass the antibiotic but small enough to block the bacteria. Once the antibiotic is introduced into the antibiotic reservoir it quickly diffuses into the microchannel region, and the susceptibility testing can begin. The fabrication of the pores can be achieved by using advanced lithography (e.g., electron beam lithography); alternatively, a porous material can be used as the top wall of the device, instead of polydimethylsiloxane (PDMS). In an exemplary embodiment, high currents (~1 mA) can be implemented to drive the bacteria in solution through the microchannel (e.g., through the chip).

In accordance with some embodiments of the invention, the bacteria can be pushed into the microchannel region efficiently by using high current/voltage. For example, this embodiment can be used to test in low concentration solutions, in which an applied high current can be used to speed up the bacteria arrival into the microchannel. In accordance with some embodiments of the invention, electrodes can be provided to form an electrical trap to trap the bacteria in the microchannel for more efficient detection. As a result, the antibiotic susceptibility testing system can be varied where electrical guiding/trapping electrodes are designed on another layer and integrated into the device.

In accordance with some embodiments of the invention, a solution of non-motile and motile bacteria can be introduced into the device from a first reservoir. A voltage can be applied causing the bacteria to be pushed to a constriction at the end of the microchannel. After the bacteria have accumulated in the constriction, a low current can be applied to measure the resistance (or voltage or current) signal fluctuations produced by presence of live bacteria in the channel.

In accordance with some embodiments of the invention, a solution of non-motile or motile bacteria can be introduced into the device from a first reservoir. A pressure-driven flow can be created causing the bacteria to be pushed to a constriction at the end of the microchannel. After the bacteria have accumulated in the microchannel, a low current can be applied to measure the resistance (or voltage or current) signal fluctuations produced by presence of live bacteria in the channel.

In accordance with some embodiments of the invention, a solution of non-motile or motile bacteria can be introduced into the device from a first reservoir. The microchannel can be coated with an adhesion-promoting surface layer. This will increase the efficiency of bacteria accumulation. Alternatively, the microchannel can be coated with a layer of specific antibody selected to trap specific bacteria such that the selected bacteria accumulate inside the microchannel. After the bacteria have accumulated in the microchannel, a low current can be applied to measure the resistance (or voltage or current) signal fluctuations produced by presence of live bacteria in the channel.

In accordance with some embodiments of the invention, the geometry of the microfluidic channel can be varied to attain more efficient detection of the bacterial movements and the signal fluctuations.

In accordance with some embodiments of the invention, the electrical measurements of the microfluidic channel may be varied to attain more efficient detection of the bacterial movements signal fluctuations.

In accordance with some embodiments of the invention, motile and non-motile bacteria can be immobilized on the channel walls; their mechanical movements and fluctuations will still modulate the electrical conductance/resistance of the microchannel. This embodiment can be used to evaluate bacteria such as staph infections.

In accordance with some embodiments of the invention, a direct current (e.g., a constant or near constant direct current) can be applied across the microchannel and the bacteria movements can be monitored as a fluctuating voltage signal or an AC voltage signal. Alternatively, a DC voltage (e.g., a constant or near constant DC voltage) can be applied across the microchannel and the bacteria movements can be monitored as electrical current signal fluctuations.

In accordance with some embodiments of the invention, a correlation measurement can be performed. In this embodiment, a second pair of electrodes can be inserted but through a separate path. The current can be applied as before through the first electrode pair. Then, the voltage fluctuations measured through electrode pair A is cross-correlated with those measured through B: $<V_A(t)V_B(t)>$. This can be used to provide a more sensitive measurement of the signal fluctuations and can be used to avoid signal artifacts from outside the microchannel region (i.e., the bacteria).

In accordance with some embodiments of the invention, radiofrequency (RF) signal measurements can be performed. As a general matter, RF signal measurements can provide a number of advantages over low-frequency measurements. First, the availability of low-noise RF amplifiers can make RF measurements more precise. Second, RF measurements will provide much larger bandwidths (much smaller time resolution). Furthermore, in these measurements, one does not need to apply a direct current through the nanochannel. Instead, one electrode can be grounded and the other can be connected to a reflectometer. This measurement can be used to determine (a complex measure of) the impedance of the nanochannel as a function of time. The imaginary part of the impedance can change more strongly than the real part (i.e., resistance), making this measurement useful for bacteria as well as other particles. Alternatively, RF signal transmission through the microchannel can be measured. In accordance with some embodiments, impedance matching (e.g., an LC tank circuit) can be used to better couple the power to the microchannel region of the circuit.

BRIEF DESCRIPTION OF THE DRAWINGS

This patent or application file contains at least one drawing executed in color. Copies of this patent or patent application publication with color drawing (s) will be provided by the Office upon request and payment of the necessary fee.

FIG. 1A shows that there are four mm-scale reservoirs connected to large channels; at the center is the tiny microchannel, FIG. 1A (inset) is a microscope image of a polydimethylsiloxane (PDMS) device, showing the tiny microchannel 120 in between reservoirs 110. FIG. 1B shows a diagram of a microfluidic transducer chip 101 in accordance with some embodiments of the invention. FIG. 1C shows a diagram of a circuit model for the microfluidic transducer chip 101 shown in FIG. 1B.

FIG. 2A exemplifies an ionic solution filling the microchannel, whereas FIGS. 2B and 2C show exemplary voltage fluctuations with the corresponding activity (e.g., movements) of bacteria in accordance with some embodiments of the invention. FIG. 2D shows exemplary voltage fluctuations with the bacteria trapped or captured to the microchannel walls in accordance with some embodiments of the invention. In FIG. 2D, the physical or chemical bond between the bacterium and the surface is modeled as a spring in accordance with some embodiments of the invention. FIG. 2E shows exemplary mean resistance increase (under a constant applied current) as the bacteria proliferate in accordance with some embodiments of the invention. FIG. 2F exemplifies a chip designed with several multiplexed microchannels connected to a reservoir to enable comparison to the measured electrical signals in the microchannel before and after administering the antibiotic in accordance with an embodiment of the invention.

FIG. 3A exemplifies a general detection approach to demonstrate the efficiency of the antibiotic susceptibility testing system in accordance with some embodiments of the invention. First, the baseline for the device and the solution can be established by measuring the signal (e.g., voltage or current fluctuations) for a predefined period (e.g. 30 sec. to 5 min or more). The measuring time can depend on the solution used and the device configuration, and some device and solution combinations may require more measurement time. The RMS value of the base signal fluctuations can be computed as a function of the measured signal (e.g., voltage or current) fluctuations for one or more predefined periods of time (e.g. over the measurement time). FIG. 3B shows approximately 10 $E.$ $coli$ bacteria cells swimming in the microchannel 120. FIG. 3C shows the voltage fluctuations recorded in the microchannel over time and that the observed increase in voltage fluctuations is bacterial activity.

FIG. 5A shows an embodiment that demonstrates the addition of an added reservoir connected to the microchannel directly. FIG. 5B shows electrodes designed and fabricated on the chip for controlling and trapping the bacteria in the microchannel region for faster and more efficient measurements in accordance with some embodiments of the invention. FIG. 5C exemplifies another variation of the antibiotic susceptibility testing system for non-motile bacteria in accordance with some embodiments of the invention, where a solution of non-motile bacteria 138 can be introduced into the device from one reservoir 110A.

FIGS. 6A, 6B and 6C show bacteria are pipetted into the top reservoir; either a pressure gradient (FIG. 6A) or an electric field (FIG. 6B) pushes them into the microchannel (FIG. 6C) where they are captured by surface chemistry, jammed into the constriction by the flow, or simply stick to the microchannel surface on their own. FIG. 6D shows a microscope image of approximately 50 $E.$ $coli$ immobilized in a tapered microchannel. The entire taper region has a height of ~1 μm, and thus confines the bacteria. Once immobilized, the bacteria do not leave the shown taper region but continue their nanomechanical movements (wiggling). FIG. 6D (inset) shows the electrostatic interaction mediated by an adhesion-promoting coating, PDL. This non-specific chemistry increases the capture efficiency, but it is not essential. Alternatively, one could use a specific surface coating (e.g., antibody) to selectively capture bacteria in the microchannel in a targeted manner. FIG. 6E shows a microscope image at $t=0$, 2 mins and 5 mins showing increasing the effective local density of bacteria by capture in the microchannel where bacteria ($S.$ $epidermidis$) are introduced into the device at $t=0$, and a flow is established by a pressure gradient. The initial concentration of the bacteria in solution is about $10^5$ colony forming units (CFU)/ml (top panel). The volume of the V-shaped (tapered) microchannel region is about $10^{-8}$ ml. After 2 minutes, the flow deposits about 10 bacteria in the microchannel, resulting in a local density of about $10^9$ bacteria/ml (middle panel). After 5 minutes, the local density goes up by another factor of two to about $2\times10^9$ bacteria/ml (bottom panel).

FIG. 7A is a schematic showing a bacterium adhered onto a surface exhibiting nanomechanical fluctuations. FIG. 7B is a schematic showing a chemical or physical bond between the bacterium and the surface that is modeled as a spring wherein the bacterium exerts a steady but random force on the spring, resulting in large amplitude (10s of nm) random vibrations FIG. 8A shows an electrostatic interaction between the channel wall, PDL, and bacteria in order to adhere bacteria on the microchannel walls in accordance with some embodiments of the invention. FIG. 8B shows the nanomechanical models of the bacteria adhered on the microchannel walls. The springs model the PDL and are electrostatic in nature, in accordance with some embodiments of the invention.

FIG. 9A shows a system according to some embodiments of the invention, where correlation measurement can be implemented, and shows another pair of electrodes inserted through separate paths in accordance with some alternative embodiments of the invention. FIG. 9B exemplifies implementing a basic radiofrequency (RF) reflectometry measurement in accordance with some alternative embodiments of the invention. FIG. 9C exemplifies implementing an alternative RF transmission measurement in accordance with some alternative embodiments of the invention.

FIG. 11 (inset) shows the cells entering the microchannel. The black data trace is the background signal before the bacteria are introduced into the microchannel.

FIG. 12A shows the electrical fluctuations in the time domain before (black baseline signal) and after (red) the cells are captured. FIG. 12B shows the power spectra of the signals shown in FIG. 12A, where the cells are captured in a tapered microchannel (FIG. 12B inset). The nanomechanical movements of the bacteria cause increased electrical fluctuations and increase in RMS signal.

FIGS. 13A-13C show antibiotic susceptibility test results from bacterial movements in human urine. FIGS. 13A and 13B show voltage fluctuations in one-minute long electrical measurements, over time, on a susceptible *E. coli* strain (FIG. 13A) and a resistant *E. coli* strain (FIG. 13B). FIG. 13C shows a bar chart of the RMS magnitude of the fluctuations of susceptible *E. coli* strain and a resistant *E. coli* strain. The "before-antibiotic" amplitudes vary from sample to sample, because they depend on the size of the bacteria population and where the bacteria are trapped in the taper.

DETAILED DESCRIPTION

Aspects and embodiments of the invention relate to an antibiotic susceptibility testing system comprising at least one reservoir into which a bacteria solution is introduced and a microfluidic channel (herein referred to as a microchannel or a nanochannel) connected to the reservoir which supplies the bacteria solution for testing. The antibiotic susceptibility testing system can be used to determine whether or not bacteria are live and viable, thus efficiently enabling antibiotic susceptibility testing of bacteria.

The antibiotic susceptibility testing system according to the invention detects bacterial activity (e.g., natural motility, viability). By using small devices (nano-scale devices), signals from a few bacteria can be detected and thus enabling detection of a much smaller bacteria population. This approach can significantly reduce the complexity and time necessary for sample testing, and hence the sample-to-answer time. The antibiotic susceptibility testing system according to the invention is based on a simple electrical (e.g., resistance or conductance) measurement. Hence, it does not require sensitive microscopy, is label free, and can be used at the clinical point of care.

Figure 1A:
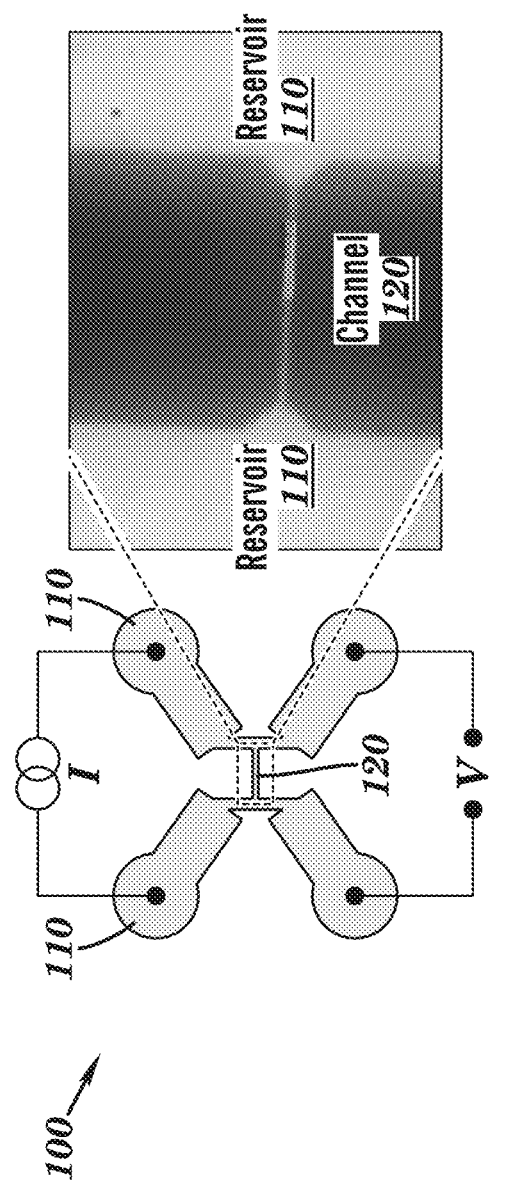
FIGS. 1A-1C shows an exemplary antibiotic susceptibility testing system in accordance with some embodiments of the invention.
Figure 1C:
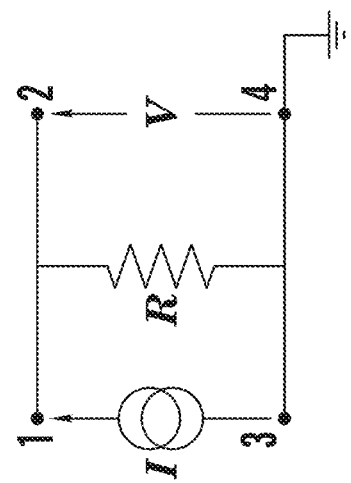
Figure 1B:
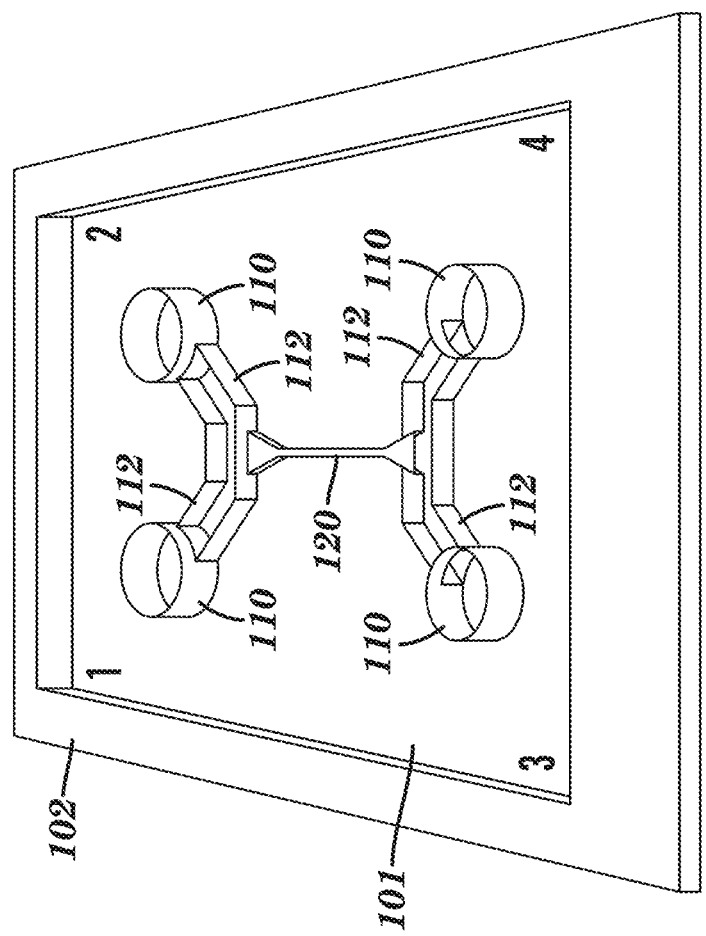

FIGS. 1A, 1B and 1C show diagrams of an antibiotic susceptibility testing system 100 in accordance with some embodiments of the invention. The antibiotic susceptibility testing system 100 can comprise at least one reservoir 110 coupled to at least one microchannel 120. As shown in FIG. 1B, the system 100 can include four mm-scale reservoirs 110. Metal electrodes for electrical measurements can be inserted into the reservoirs 110 or integrated in to them during fabrication. The microchannel 120 can be at the center of the system 100. Saline or bacteria solutions (e.g., an ionic solution such as urine, a buffer solution or other biological matrix) can be introduced by pipetting or pumping liquid into at least one of the reservoirs 110. The liquid solution can be wicked (e.g., via capillary action) or pumped (e.g., via pressure) into the microchannel 120. FIG. 1A shows (inset) a microscope image of a polydimethylsiloxane (PDMS) device, showing the tiny microchannel 120 in between reservoirs 110. The voltage and/or current can be measured by a signal measuring device V (e.g., an oscilloscope, a digital signal processor, an analog signal processor, an ammeter, a voltmeter, or a computer) and the fluctuation in voltage (or current) can be used to detect the presence of live bacteria. The signal measuring device V can be configured to store and display the amplitude of the signals over time (e.g., a graph, chart, running average, peak detection, etc.). The signal measuring device V can include a computer or microprocessor and associated memory that stores programs to be executed that can process the signal (e.g., the resistance, voltage, and/or current) to determine the presence of live bacteria in the channel as a function of the electrical signal fluctuations measured in the microchannel 120.

FIGS. 1B and 1C show diagrammatic views of an antibiotic susceptibility testing system 100 in accordance with some embodiments of the invention. FIG. 1B shows a diagram of a microfluidic transducer chip 101 in accordance with some embodiments of the invention. FIG. 1C shows a diagram of a circuit model for the microfluidic transducer chip 101 shown in FIG. 1B. The microfluid transducer chip 101 can be formed from PDMS and bonded onto a glass substrate 102. In accordance with some embodiments of the invention, microfluidic transducer chip 101 can include four mm-scale reservoirs 110 connected to 100-μm-depth channels 112. At the center, the tiny microchannel 120 connects the channels 112. Preferably, the microchannel 120 has cross-sectional dimensions comparable to the size of the bacteria in the range from 100 nanometers-several micrometers (e.g, 3000 nanometers) on a side. In accordance with some embodiments of the invention, the cross-sectional size of the microchannel is in the range from 1-2 micrometers by 1-2 micrometers. In accordance with some embodiments of the invention, the cross-sectional dimensions of the microchannel can be in a range from sufficiently small relative to the smallest dimensions of the bacteria to be detected to enable the bacteria to either just pass through the microchannel or become jammed into the microchannel to sufficiently large such that the presence of live bacteria cause detectible changes in the resistance through the microchannel In operation, a current source I can be used to provide a constant-amplitude electric current that is injected into reservoir 1 and flows through the nanochannel 120 to the electrical ground (reservoirs 3 and 4). The voltage drop between reservoirs 2 and 4 is measured by a voltage measuring device V (e.g., an oscilloscope, a digital signal processor, an analog signal processor, a voltmeter, a lock-in amplifier, or a computer). Alternatively, a constant amplitude voltage source may be connected across the microchannel (reservoirs 1 and 3). Here, the current flowing through the microchannel may be detected using a current measuring device (e.g., an ammeter, a multimeter, a lock-in amplifier, a current amplifier, or a computer). In accordance with some embodiments of the invention, the contact resistances in the system do not alter the measured signals. The electrical impedance of the microchannel 120 is dominated by its resistance at the low-frequencies used and the effects of the parasitic capacitances are thus negligible.

FIGS. 2A-2E show diagrammatic views of a microchannel 120 according to some embodiments of the invention. The microscopically small channel 120 can be filled with an ionic aqueous solution, such as phosphate-buffered saline (PBS), urine, or other biological fluid that can sustain the bacteria to be tested. The effective channel cross-section is typically on the order of several micrometers (e.g., 1-2 micrometers by 1-2 micrometers) in diameter or smaller (e.g., a rectangular cross-section of 1 micrometer by 1 micrometer; also see FIG. 3B, FIG. 6D, FIG. 6E, FIG. 14 and FIG. 15 for representative dimensions and geometries) and is herein referred to as the microchannel 120. The microchannel length can be longer (e.g., 50-200 micrometers). The microchannel 120 can be connected to larger mm-sized reservoirs at one or both ends, interfacing with standard microfluidic elements.

Figure 2A:
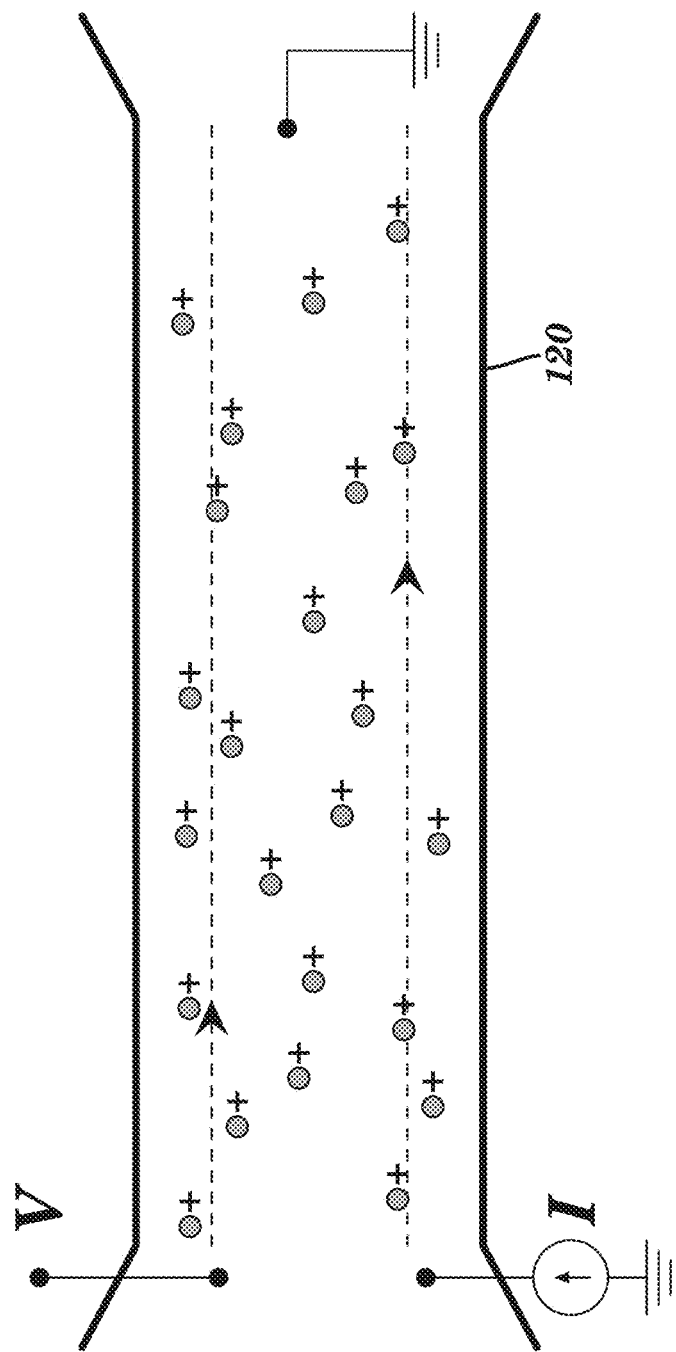
FIGS. 2A-2F show diagrammatic views of a microchannel 120 according to some embodiments of the invention, showing how the chip 100 can be used as a transducer that converts bacterial viability (e.g., motion and growth) into electrical signals using different modalities.
Figure 2B:
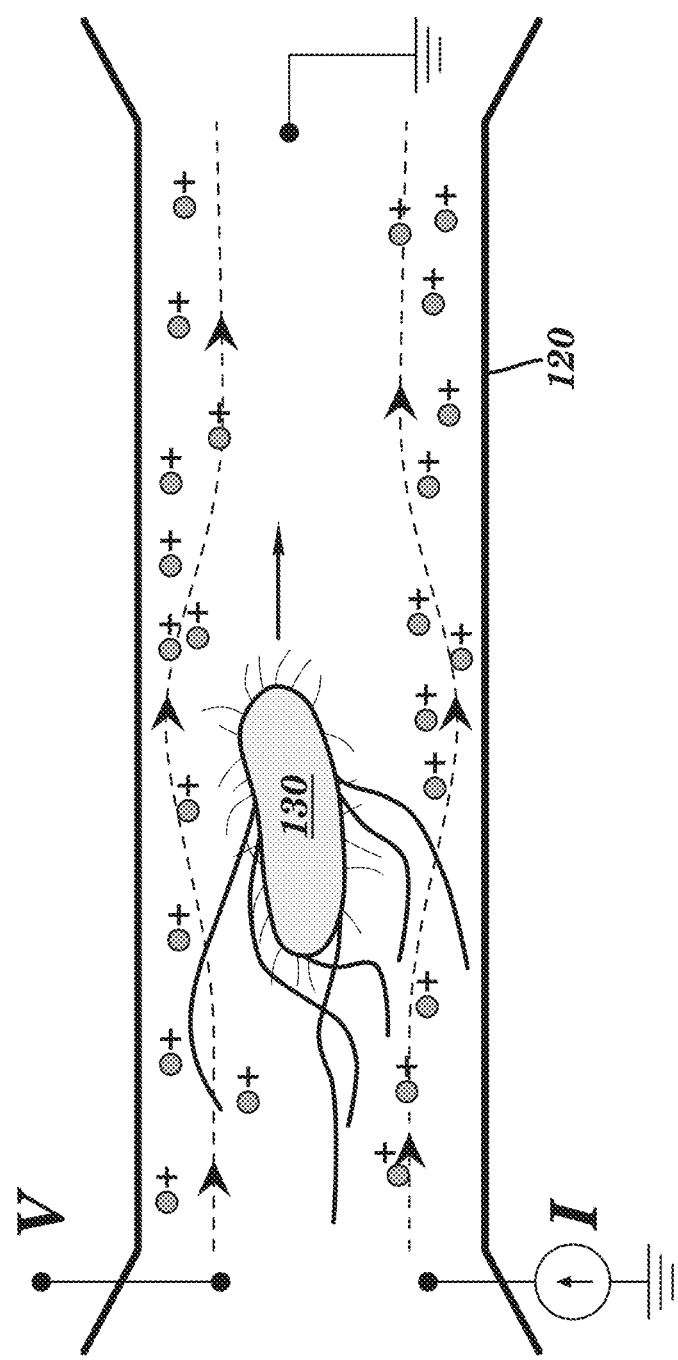
Figure 2C:
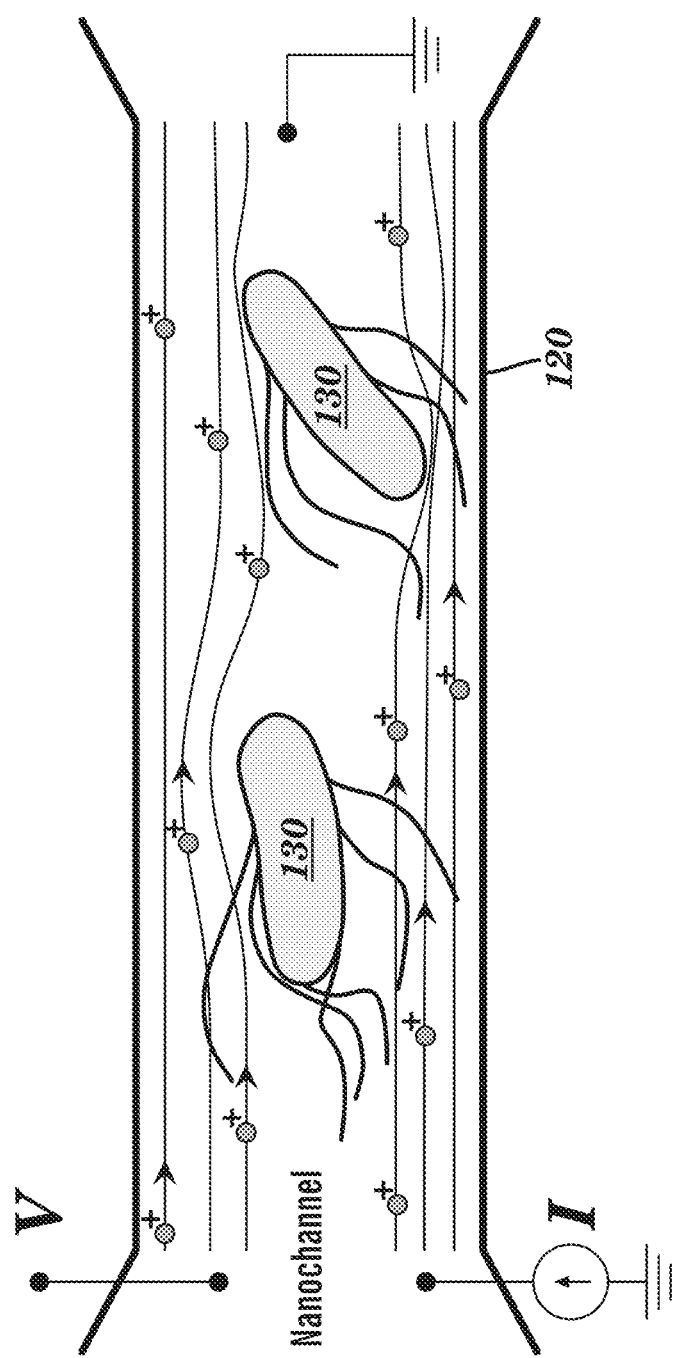

As shown in FIG. 2A, prior to the introduction of any bacteria in the solution, the intrinsic electrical noise in the circuit can be monitored and determined. These intrinsic-noise-based electrical fluctuations can be used to establish a baseline (e.g., a noise floor) of the measurement of bacterial activity. As shown in FIGS. 2B and 2C, bacterial activity (e.g., bacteria 130 moving (e.g., swimming) into the channel from the reservoirs at one or both ends) changes the effective channel diameter and causes changes to the electrical properties of the microchannel (e.g., the electrical resistance of the microchannel). In other words, the effective cross-sectional area of the nanochannel 120 for conducting ions is modulated by the presence (or absence) of bacteria 130 in the microchannel 120. These electrical resistance fluctuations directly correspond to bacterial activity. For example, if the bacteria 130 are dead, these fluctuations cease and effectively return to the intrinsic level.

FIG. 2A shows an ionic solution in the nanochannel 120. In an exemplary embodiment, ions flow through a nanochannel 120 under an imposed electric potential resulting in a measurable electric current I. The voltage drop V may be measured as a function of time, and the electrical resistance is R=V/I. In accordance with some embodiments of the invention, as shown in FIG. 2B a bacterium 130 enters the microchannel 120, the electrical resistance increases due to the reduction in the effective cross-section of the nanochannel 120 diameter. This results in a voltage increase under constant current. As a bacterium exits the microchannel 120, the resistance decreases due to increase (e.g., restoration) of the cross-section of the microchannel. This results in voltage fluctuations, even though the time averaged value of the voltage may be stable. The exemplary voltage fluctuations are shown in FIGS. 2B and 2C with the corresponding fluctuation in bacterium.

Figure 2D:
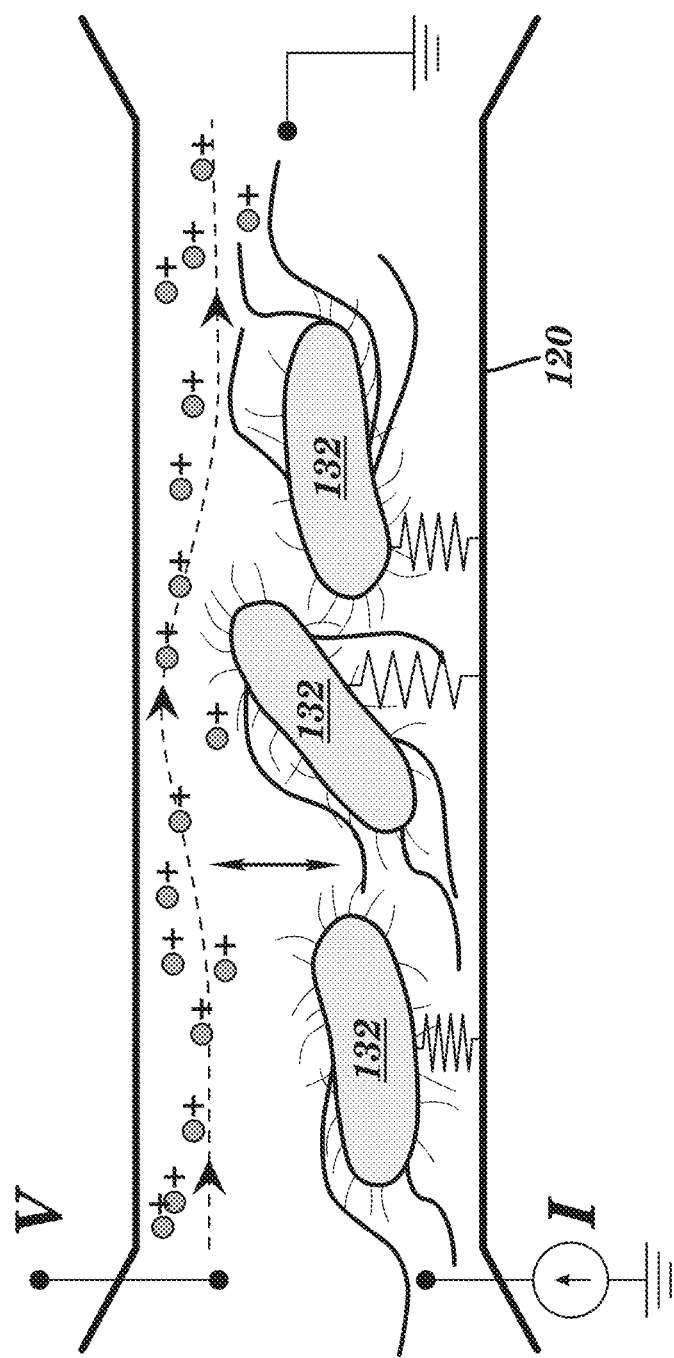

FIG. 2D shows an ionic solution in the microchannel 120 according to some embodiments of the invention, however, all or a portion of the walls of the microchannel 120 are treated such that the bacteria cells 132 become attached, adhered or tethered to the treated walls of microchannel 120. Alternatively, the cross-section of microchannel can be small such that the cells become physically stuck or jammed in the microchannel. In this embodiment, the nanomechanical movements (e.g., wiggling) of the bacteria 132 cause corresponding fluctuations in the electrical resistance, similar to the situation described above. The resistance fluctuations arise because the bacterial movements modulate the electrical resistance through the channel. When the bacteria 132 die, the resistence fluctuations decrease due to the decrease in the movements of the bacteria and the modulations of the effective cross-section of the microchannel 120.

Figure 2E:
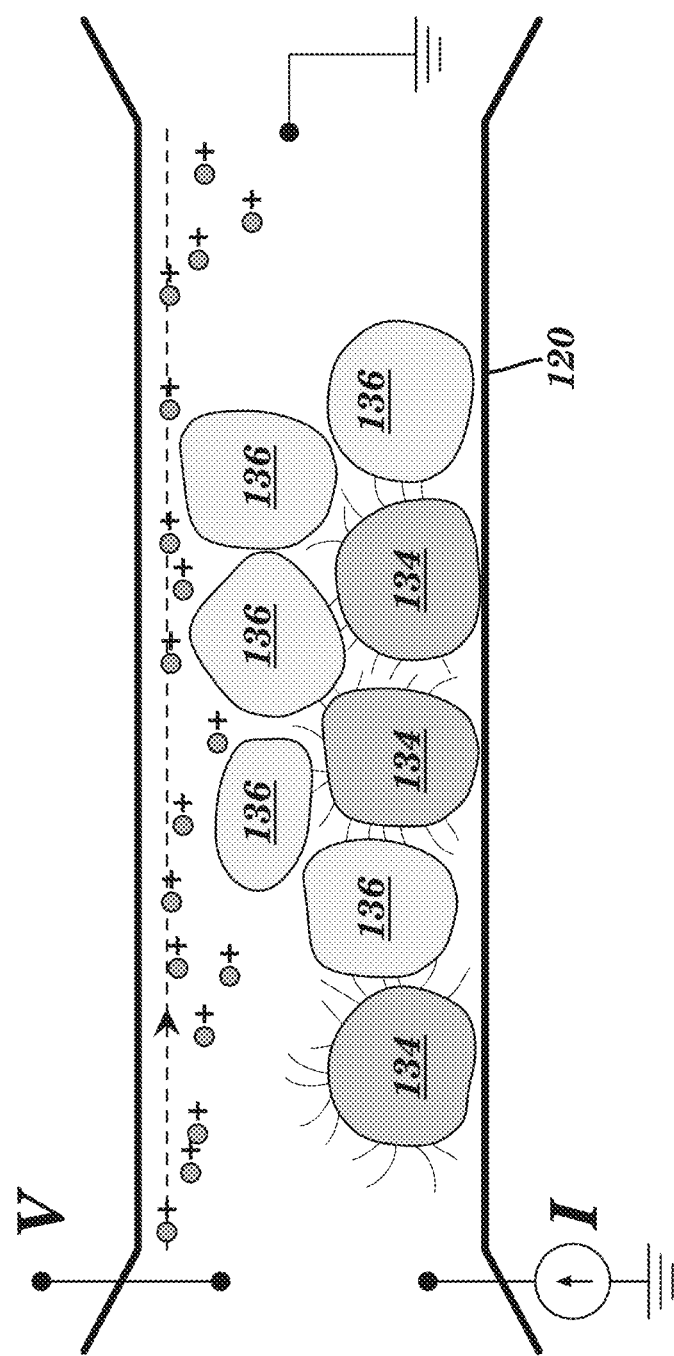

FIG. 2E shows an ionic solution in the microchannel 120 according to some embodiments of the invention, however, all or a portion of the walls of the microchannel 120 are treated such that the bacteria cell 134 become attached, adhered or tethered to the treated walls of microchannel 120. In accordance with some embodiments of the invention, the bacteria 134 proliferate in the microchannel 120 and new bacteria cells 136 grow in the microchannel and change the mean resistance by constricting the microchannel 120. The mean or average resistance can be determined as a function of the measured resistance through the microchannel. The measured resistance can be determined (e.g., using ohm law) by applying a constant voltage to microchannel and measuring the current over time or applying a constant current to the microchannel and measuring the voltage over time.

Figure 2F:
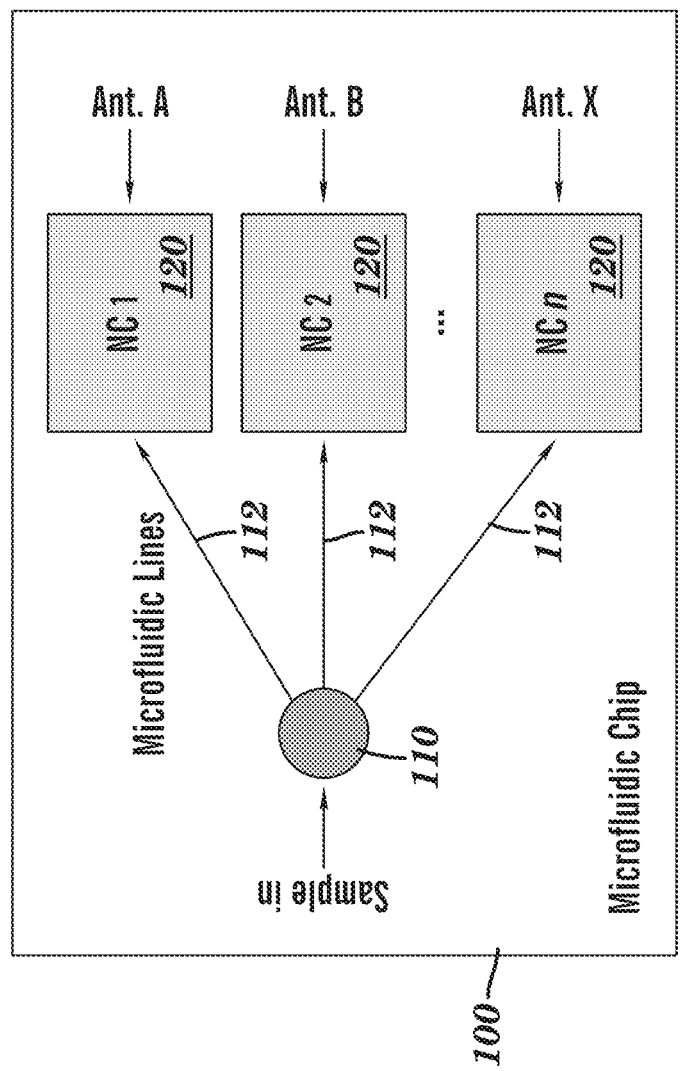

In some embodiments, the measured electrical signals (e.g., V and R) in the microchannel 120 are compared before and after administering the antibiotic. Referring now to FIG. 2F, in accordance with some embodiments of the invention, a chip 100 can be designed with several microchannels 120 connected to a reservoir 110. The measurement circuit can be multiplexed in the device such that it can read out the resistances of each of the microchannels at the same time. The sample can be delivered/pipetted into reservoir 110 of the chip 100, which first divides the sample using, for example, gravity feed or a microfluidic pump and channels. In other words, the sample is initially aliquoted into the several microchannels. This step can be automated using programmable microfluidics. Once the sample is delivered into the microchannels in parallel, the measurement procedure can be run as discussed, but with each microchannel being exposed to a different antibiotic.

In accordance with some embodiments, a signal processing system can be used to measure the voltage and/or current signal fluctuations. The signal fluctuations of the base solution before the bacteria are added can be measured and used as a baseline signal to evaluate the signal fluctuations after live bacteria are added. The signal processing system can monitor signal fluctuations by measuring the amplitude of the signal (e.g., over the baseline signal) to detect live bacteria in the microchannel. These higher amplitude signal fluctuations should become reduced after the introduction of the antibiotic and the signal should return to the base level. The signal processor can include a computer processor and associated memory that stores computer programs that can be executed by the processor to process the signals and identify the fluctuations and change in amplitude to indicate the presence of live bacteria in the microchannel, as well as the susceptibility of the bacteria to antibiotic treatment by the reduction in the higher amplitude signals.

In accordance with some embodiments of the invention, the microchannel 120 can be fabricated using silicone (PDMS) and other biocompatible materials using well established processing steps. In accordance with some embodiments of the invention, the microchannel 120 can be positioned between two (or more) mm-sized reservoirs with exemplary linear dimensions of w×h×l≈2 μm×2 μm×100 μm. In alternative embodiments, the linear dimensions may be varied to attain more efficient detection of the motility and the fluctuations based on the size of the bacteria to be evaluated. When motile bacteria in solution are introduced into the antibiotic susceptibility testing system 100 via the reservoirs 110 at one or both ends, the bacteria swim randomly and some enter the microchannel 120 region.

FIGS. 2A-2F show how the chip 100 according the various embodiments of the invention can be used as a transducer that converts bacterial viability (e.g., motion and growth) into electrical signals using different modalities. There are negligible electrical fluctuations in the microchannel without any bacteria (FIG. 2A) and it behaves as an electrical resistor, which has time-independent resistance. In accordance with some embodiments of the invention, planktonic motile bacteria 130 swimming in the microchannel generate fluctuations (FIGS. 2B and 2C). In accordance with some embodiments of the invention, bacteria 132 captured/immobilized inside the microchannel also generate substantial electrical fluctuations owing to their random movements (wiggling or oscillations), as shown in FIG. 2D. In this embodiment, bacteria 132 can become tethered to the microchannel surface by adhesion-promoting coatings and/or simply adhere to the surface by themselves and/or become jammed into the tight microchannel. Thus, the random movements of bacteria 132 modulate the microchannel diameter (FIG. 2D), thereby resulting in detectable electrical signals. Any changes in bacterial 132 viability and movements are sensitively captured in the electrical signal. In accordance with some embodiments of the invention, the chip 100 can be used to detect bacterial viability from proliferation. As shown in FIG. 2E, the microchannel device can be used as an ultrasensitive culture medium. As surface-immobilized bacteria 134 proliferate (e.g., bacteria cells 136 grow) in the microchannel, the time-averaged (dc) voltage signal increases under constant electric current proportionally to the number of cells in the microchannel. This is because the cells simply obstruct the electric current flow and increase the mean (average) electrical resistance.

More insight can be gained from the circuit diagram (FIG. 1C) and the related equations. Using the circuit diagram in FIG. 1C, Ohm's Law can be applied:

$$V_{dc} + \delta V(t) = I_{dc} \times [\overline{R} + \delta R(t)] \quad (1)$$

where $I_{dc}$ is a fixed current and $\overline{R}$ is the time-averaged (dc) electrical resistance of the microchannel. The instantaneous movements of the bacteria change the electrical resistance by $\delta R(t)$. Thus, the fluctuating component of the signal that corresponds to bacterial activity (e.g., live movements) is $\delta V(t) = I_{dc} \times \delta R(t)$. Finally, the time-averaged (dc) signal, $V_{dc} = I_{dc}\overline{R}$, is proportional to the number of cells inside the microchannel due to the obstruction of the current by the cells. The method thus provides both the movement signal and the number of bacteria in the microchannel. Alternatively, the system can apply a dc voltage across the microchannel and measure the current fluctuations due to the changes in the resistance of the microchannel. The equation given by Ohm's Law then becomes:

$$I_{dc} + \delta I(t) = V_{dc}/[\overline{R} + \delta R(t)] \quad (2)$$

Similar to above, the fluctuating component of the signal that corresponds to bacterial activity (e.g., live movements) is $\delta I(t) = V_{dc} \times \delta R(t)/\overline{R}^2$. As above, the time-averaged signal that corresponds to the number of cells inside the microchannel is: $I_{dc} = V_{dc}/\overline{R}$. As a person having ordinary skill would understand, the analyses presented in Equations 1 and 2 are valid for alternating current (AC) signals as well. In the case of AC signals, the amplitudes of the current and voltage would be included in the equations.

Figure 3A:
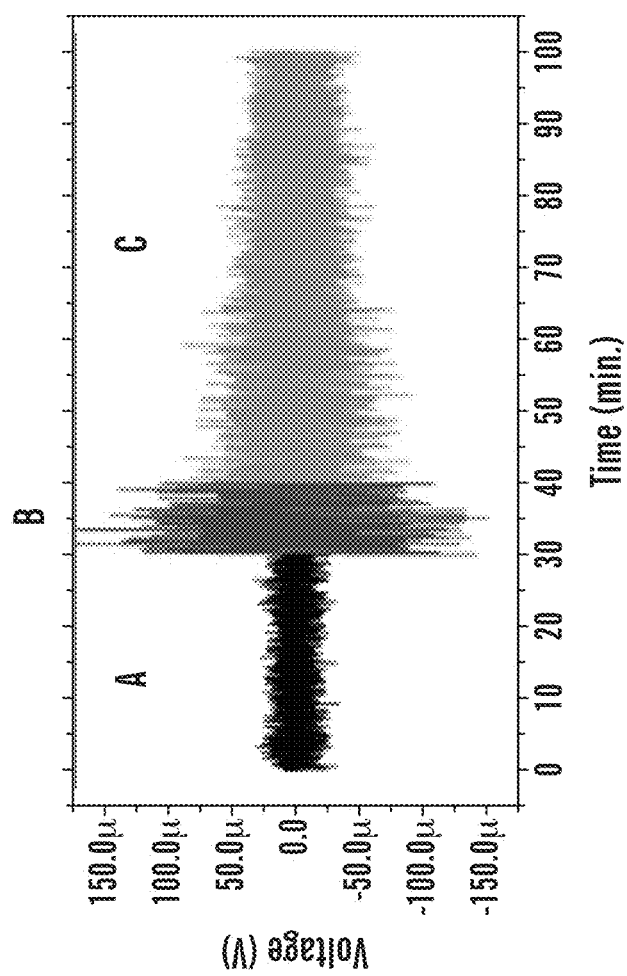
FIGS. 3A-3C show results from exemplify testing performed to demonstrate the efficiency of the antibiotic susceptibility testing system in accordance with some embodiments of the invention.

FIG. 3A exemplifies a general detection approach to demonstrate the efficiency of the antibiotic susceptibility testing system in accordance with some embodiments of the invention. First, the baseline for the device and the solution can be established by measuring the signal (e.g., voltage or current fluctuations) for a predefined period (e.g. 30 sec. to 5 min or more). The measuring time can depend on the solution used and the device configuration, and some device and solution combinations may require more measurement time. The RMS value of the base signal fluctuations can be computed as a function of the measured signal (e.g., voltage or current) fluctionations for one or more predefined periods of time (e.g. over the measurement time). This is shown as the black signal (area A) in FIG. 3A. Next, bacteria will be introduced into the device. After a few minutes (e.g., 1-3 min.) of settling time, signal data can be collected for a predefined period (e.g. 2 min. to 10 min.) and RMS value of the signal fluctuation caused by the active bacteria can be computed as a function of the collected signal data for one or more predefined periods of time. Depending on the concentration and the character of the bacteria, the settling time and signal data collection time can be longer or shorter. This is shown as the red signal (area B) in FIG. 3A. The RMS magnitude of the black signal in area A (e.g, before the bacteria were added) and the RMS magnitude of the red signal in area B (e.g., after the bacteria were added) can be compared to determine the signature of the live bacteria. Depending on the nature of the bacteria, the RMS signal magnitude of the red signal (area B) is expected to be approximately 1.2 to 50 times larger than the base amplitude (e.g., the black signal in area A). See also, FIGS. 11, 12, and 13. The ratio of the active bacteria signal (e.g., red signal in area B) to base signal (e.g., the black signal in area A) can provide a signature value for the viability of the bacteria and can be used to set a threshold for detecting the efficacy of an antibiotic treatment for the bacteria being evaluated. For example, after the baseline and bacteria signals are measured and RMS values determined, antibiotics can be administered, and the fluctuations can be measured over a predetermined amount of time, the green signal (area C) in FIG. 3A. The RMS value as a function of (wait) time can be computed in order to determine a measure of the susceptibility of the bacteria to the antibiotic treatment. In accordance with some embodiments of the invention, the antibiotic can be considered effective if the RMS signal amplitude returns to the baseline amplitude (or within 10% of the baseline amplitude) after a certain time interval. The length of the green data trace (e.g., area C) shows that some time is required to evaluate the antibiotic's effect on the bacteria as the antibiotic kills the bacteria, the signal fluctuation should return to or near the baseline level. The length of time it takes for the signal fluctuation to return to the base level will vary depending on the antibiotic and its interaction with the bacteria.

As a person having ordinary skill will appreciate, different bacteria and different antibiotics may produce different RMS magnitudes (e.g., compared to the data in the figure) and may require longer or shorter time periods to stabilize. For example, some types of non-motile bacteria may produce different signal fluctuation amplitudes and RMS amplitude values. Also different antibiotics can take more or less time to kill the bacteria and the time can vary depending on environmental factors, such as temperature, pH and concentration (of the solution, bacteria, and/or the antibiotic).

Figure 3B:
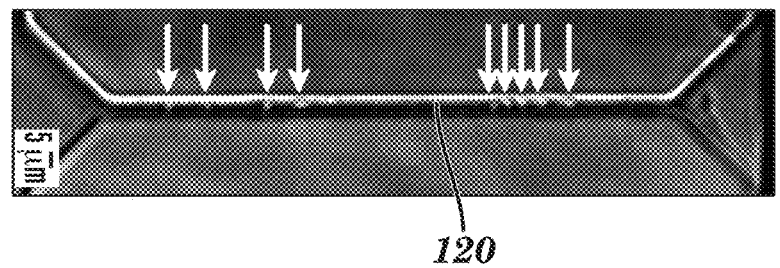
Figure 3C:
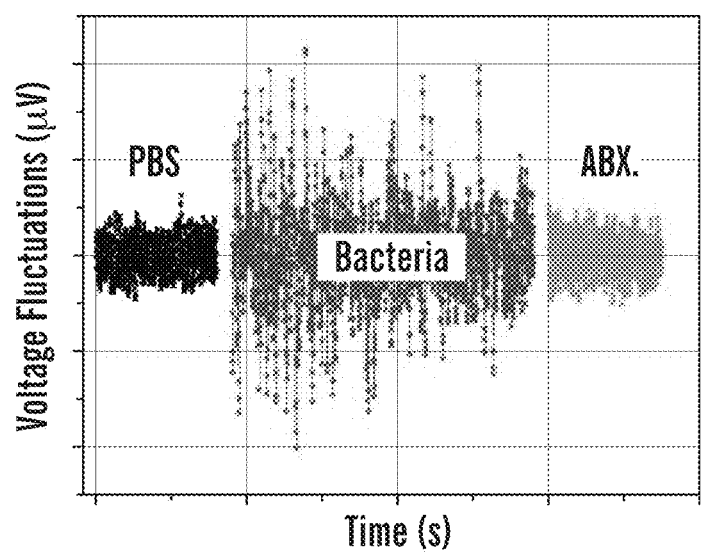

FIGS. 3B and 3C show testing performed to demonstrate the efficiency of the antibiotic susceptibility testing system 100 according to some embodiments of the invention. FIG. 3B shows approximately 10 $E.$ $coli$ bacteria cells swimming in the microchannel 120. FIG. 3C shows the voltage fluctuations recorded in the microchannel over time. The microchannel was prepared and filled with a phosphate-buffered saline (PBS) and the voltage fluctuations were measured for approximately 10 minutes. As shown in FIG. 3C, the area labeled PBS shows the initial average resistance of the channel filled with PBS (e.g., approximately 3 M$\Omega$) and the baseline voltage fluctuations are shown. Next, a solution of PBS containing live $E.$ $coli$ was then pipetted into the reservoirs on both ends of the microchannel. The concentration of $E.$ $coli$ was approximately $10^8$ cells/ml. This $E.$ $coli$ solution changed the measured average resistance by only 1%; in other words, the resistance was still dominated by the ions in the solution. However, as shown by the center section (labeled Bacteria) in FIG. 3C, the magnitude of the voltage fluctuations increased significantly. The signal fluctuations shown in the center section (labeled Bacteria) of FIG. 3C corresponds to the observed presence of approximately 10 $E.$ $coli$ cells in the microchannel 120 (shown in FIG. 3B labeled with arrows). Finally, a small volume of antibiotic solution was pipetted into the reservoirs of the device; this did not change the overall electrical resistance significantly. However, as shown in FIG. 3C in the area labeled ABX, the antibiotic was effective against the bacteria causing the fluctuations to return to the baseline uV voltage fluctuation level after approximately 10 min of administering the antibiotic.

The data in FIG. 3C shows that the source of the observed increase in the voltage fluctuations is bacterial activity. It is noted that the average electrical resistance in the device (i.e., the microchannel 120) stays about the same throughout the experiment and is dominated by the ionic solution. In these experiments performed with motile bacteria, the microchannel 120 becomes partially "clogged," and the ionic current in the channel is strongly modulated by the bacteria swimming in the microchannel 120 (FIG. 3C). This is because the cross-section of the microchannel 120 is comparable to the size of a single cell of $E.$ $coli$ (200 nm×200 nm×2 mm). Bacterial cells remained intact after the administration of the antibiotic (Kanamycin), but their activity stopped. This is supported by the notion that bacterial activity is the source of the observed signals: dead bacteria move only due to Brownian motion, which results in mean-square displacements that are smaller by orders of magnitude. This small Brownian motion is either not registered in our measurements or can be positioned below the noise floor.

To further evaluate the system, further experiments were conducted and data using different bacteria concentrations were collected. The microchannels and other experimental conditions were kept nominally identical (e.g., linear dimensions, concentration of PBS solutions). Regardless, there were slight differences in some of the measured parameters because of unavoidable statistical deviations in the fabrication process. The standard deviation, Go, of the baseline fluctuations shifted slightly from device to device (by roughly 30%). Therefore, each experiment was normalized with its own Go. Provided below is Table 1, detailing the results of the experiments with $E.$ $coli$. A total of 14 experiments were performed. Each entry is an average of 3-4 experiments. The first column is the concentration of bacteria. The second column R is the average resistance measured during the experiment using 1 nA of electrical current. The third column is the standard deviation, Go, of the baseline fluctuations (e.g., voltage) without any bacteria in the device. Note that Go shifts slightly from experiment to experiment. The fourth column is the standard deviation GB of the fluctuations (e.g., voltage) with bacteria.

TABLE 1

| Concentration (CFU/ml) | R (M$\Omega$) | $\sigma_0$ (V) | $\sigma_B$ (V) | $\sigma_B/\sigma_0$ |
|---|---|---|---|---|
| $1.0 \times 10^8$ | 3.0 | $5.7 \times 10^{-6}$ | $13.1 \times 10^{-6}$ | 2.3 |
| $2.3 \times 10^8$ | 2.8 | $4.2 \times 10^{-6}$ | $10.1 \times 10^{-6}$ | 2.4 |
| $3 \times 10^8$ | 2.9 | $4.4 \times 10^{-6}$ | $12.6 \times 10^{-6}$ | 2.9 |

Table 1 displays representative data along with the ratio of the standard deviation, $\sigma_B$, of the fluctuations with bacteria to Go measured in the same device, i.e., $\sigma_B/\sigma_0$. The higher bacteria concentration in the reservoirs corresponds to stronger fluctuations in the measured potential through the microchannel. More bacteria appear to enter the microchannel 120 region when a higher bacteria concentration is present in the reservoir. The relationship between the increase in the fluctuations and bacteria concentration does not appear to be linear and is probably a function involving other factors.

Figure 4:
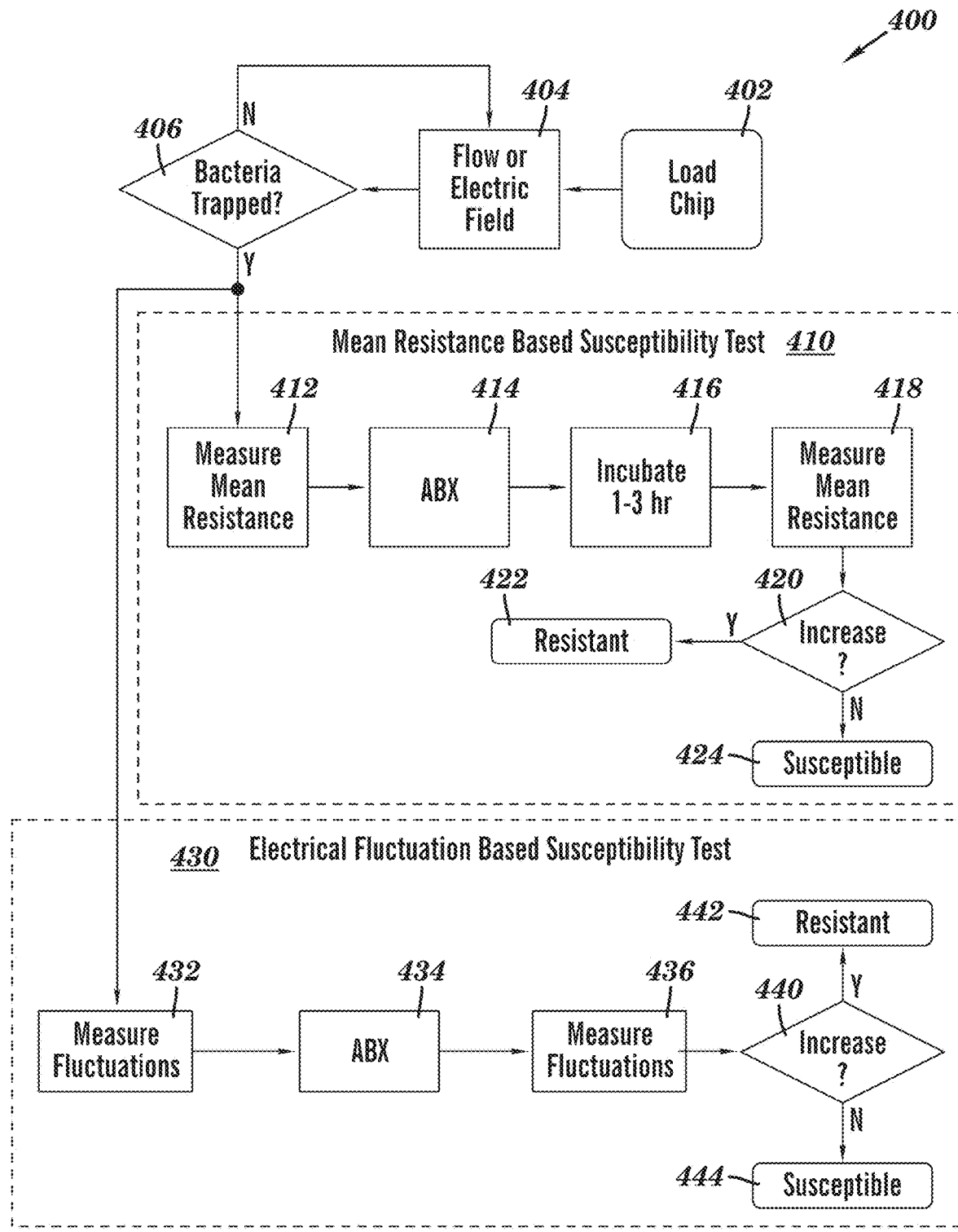
FIG. 4 shows an example of a workflow for antibiotic susceptibility testing including electrical fluctuation based susceptibility testing and mean resistance based susceptibility testing, in accordance with some embodiments of the invention.

FIG. 4 shows a workflow for antibiotic susceptibility testing according to some embodiments of the invention. In this method, bacteria are first captured/immobilized in the microchannel. Then, their viability is detected from electrical measurements under administered antibiotics. The system according to the invention can be used to provide two possible and complementary approaches for bacteria viability assessment (and hence antibiotic susceptibility testing). In the mean-resistance-based approach, growth or proliferation is detected (FIG. 2E). In the fluctuation-based approach, viability is determined from movements (FIG. 2D).

FIG. 4 shows a flow chart of a method 400 for antibiotic susceptibility testing according to some embodiments of the invention. The method 400 can include a Mean Resistance based Susceptibility Test 410 and/or an Electrical Fluctuation based Susceptibility Test 430. The method 400 can include, at 302, loading the reservoir 110 of one or more chips (e.g., chip 101) with an ionic solution and bacteria to be tested. At 404, fluid pressure and/or an electric field can be used to move bacteria into the microchannel 120, wherein the bacteria become trapped, captured or immobilized in the microchannel 120. The system can determine that the bacteria are trapped, captured or immobilized by monitoring the mean resistance signals (e.g., as bacteria are trapped, the mean resistance value increases as explained above in Equation 1). At 406, the system can determine the mean resistance value and wait a period of time and determine the mean resistance value again and compare the two signals to see if they are different by more than a predefined threshold amount. If the mean resistance values do not differ by more than the predefined threshold amount (e.g., the N or No condition, the bacteria are trapped condition is not true), the system continues to cause the bacteria to flow into the microchannel and then returns to 406 to determine the the mean resistance values another time and compares it to the mean resistance values of the previous signal. At a later time, the subsequent mean resistance values will be greater than the previous the mean resistance values signal by the predefined threshold amount (and the Y or Yes, bacteria are trapped condition becomes true), and at that point either the Mean Resistance based Susceptibility Test 410 or the Electrical Fluctuation based Susceptibility Test 430, or both can be initiated.

After the bacteria are trapped, for the Mean Resistance based Susceptibility Test 410, at 412, the baseline mean (average or time-averaged measured resistance through the channel) resistance can be measured for a predefined period of time. The baseline mean can be determined as a function (e.g., the average or time-average) of the measured resistance through the channel for two or more points in time. After the baseline mean resistance is determined, at 414, the antibiotic is added to the solution, either via one of the reservoirs 110 or directly to the microchannel 120 and, at 416, the solution containing the bacteria and the antibiotic is allowed to incubate for a predefined period of time (e.g., 1-3 hours, although shorter or longer periods can be used). After the expiration of a predefined period of time, at 418, the mean resistance is determined (e.g., as a function of the measured resistance through the channel for two or more points in time) and, at 420, the mean resistance is compared to the baseline mean resistance. If the mean resistance is greater than the baseline mean resistance, then the bacteria can be considered resistant to the antibiotic at 422. If the mean resistance is not greater than the baseline mean resistance, the bacteria can be considered susceptible to attack by the antibiotic at 424.

After the bacteria are trapped, for the Electrical Fluctuation based Susceptibility Test 430, at 432, the system measures the fluctuations of the electrical signals (e.g., voltage or current) to determine a baseline RMS signal level (e.g., the RMS level determined as function of the measured signal fluctuations). Next, at 434, the antibiotic is added to the solution, either via one of the reservoirs 110 or directly to the microchannel 120. Next, at 436, the (RMS) fluctuations of the electrical signal (e.g., voltage or current) are measured again and an RMS level can be determined as a function of the measured signal fluctuations, and, at 440, the RMS level of the fluctuations of the electrical signal can be compared to the baseline RMS signal level. If the RMS level of the fluctuations of the electrical signal is greater than the baseline signal RMS level, then the bacteria can be considered resistant to the antibiotic at 442. If the RMS level of the fluctuations of the electrical signal is not greater than the baseline RMS signal level, the bacteria can be considered susceptible to attack by the antibiotic at 444.

Figure 5A:
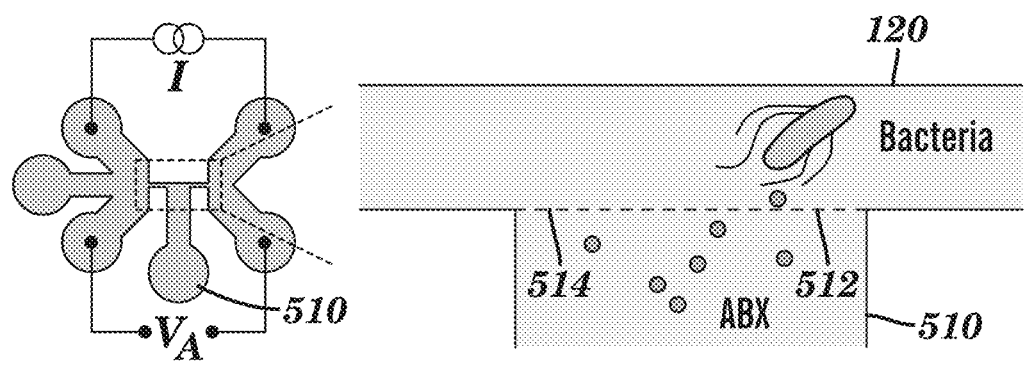
FIGS. 5A-5C show different geometries variations of the antibiotic susceptibility testing system in accordance with some embodiments of the invention.
Figure 5B:
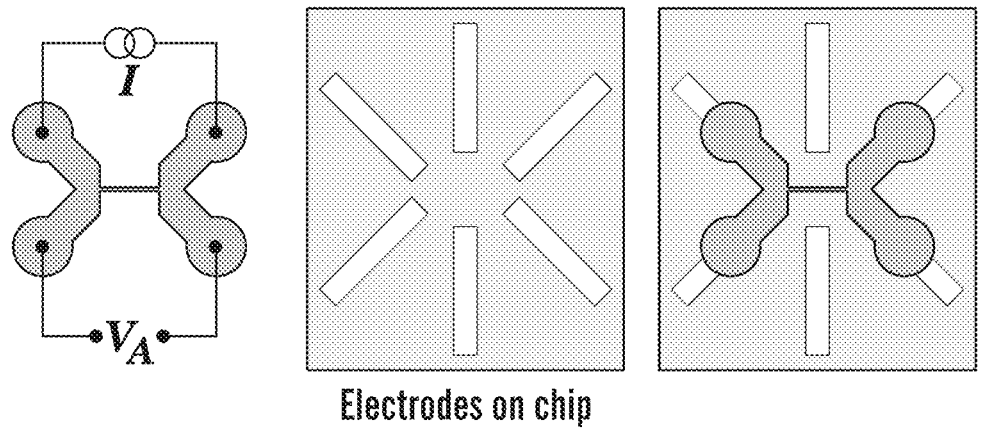
Figure 5C:
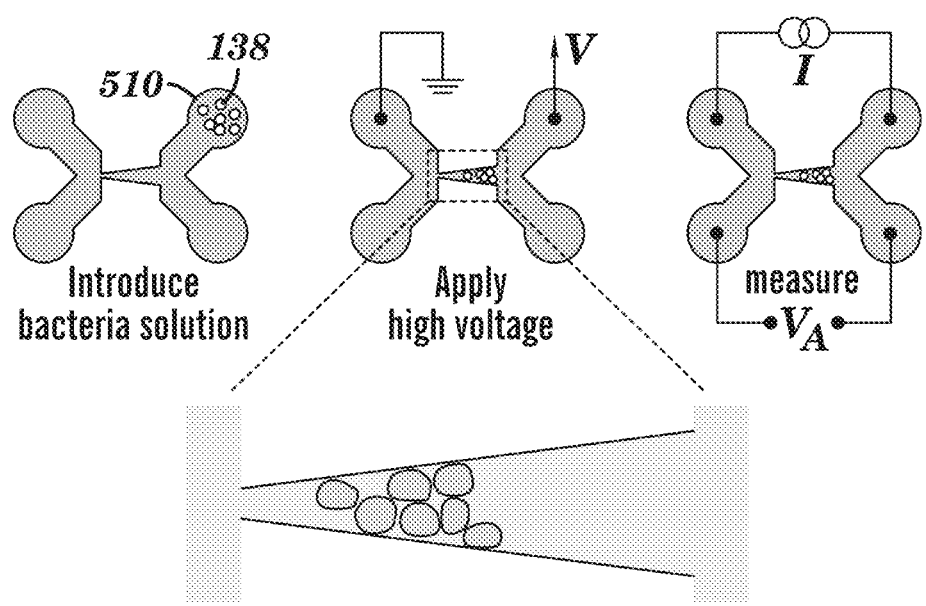

In accordance with some embodiments of the invention, the geometry of the microfluidic channel can be varied to attain more efficient detection of the motility and the fluctuations. A variation for antibiotic susceptibility testing is shown in FIGS. 5A, 5B, and 5C. In previous studies, antibiotic diffusion from reservoirs takes time. An object of the present embodiment is to reduce or eliminate unnecessary latency. As shown in FIG. 5A, an embodiment demonstrates the addition of an antibiotic reservoir 510 directly connected to the microchannel 120. Furthermore, the pores 514 in the wall between the reservoir and the microchannel are large enough that antibiotic molecules can pass into the microchannel, but small such that bacteria cannot pass into the antibiotic reservoir 510. Note that the resistance measurement as noted before is not perturbed in this variation. Once the antibiotic is introduced into the reservoir it quickly diffuses to the microchannel 120 region, and the susceptibility testing can be initiated. The fabrication of the pores 514 can be achieved by using advanced lithography (e.g., electron beam lithography); alternatively, a porous material can be used as the top wall of the device, instead of PDMS. The antibiotic (ABX) can reach the bacteria in the microchannel 120 quickly if pores 514 are made on the microchannel wall 512, connecting it to a reservoir 510 of antibiotics.

In addition, high currents (e.g., from 250 nA to 10 mA) can be used to drive bacteria in the solution through the device. In particular, the bacteria can be pushed into the microchannel region (e.g., using the high current/voltage signal). This can be useful in testing low bacteria concentration solutions—the applied high current can be used to speed up the bacteria migration into the microchannel region. In accordance with some embodiments of the invention, an electrical trap can be used to trap the bacteria in the microchannel region for efficient detection. For example, FIG. 5B shows an example of the system 100 configured with electrical guiding/trapping electrodes formed on a substrate that supports the microchannel and the reservoirs of the antibiotic susceptibility testing system. As shown in FIG. 5B, electrodes can be designed and fabricated on the chip for controlling and trapping the bacteria in the microchannel region for faster and more efficient measurements.

In accordance with some embodiments of the invention as shown in FIG. 5C, a solution of non-motile bacteria 138 can be introduced into the device from one reservoir 110A. A relatively high voltage V can be applied to move the non-motile bacteria to the constriction at the left end of the microchannel. Once the bacteria 138 are accumulated as shown, the high voltage is turned off and a low constant current can be actuated for use in measuring the fluctuations in voltage. In accordance with some embodiments of the invention, the basic electrical fluctuation measurement can be performed as follows: 1) a constant direct current can be induced through the microchannel and the ensuing alternative current fluctuations in voltage can be measured and monitored. Alternatively, a constant DC voltage can be applied across the microchannel and current fluctuations can be measured and monitored.

Figure 6A:
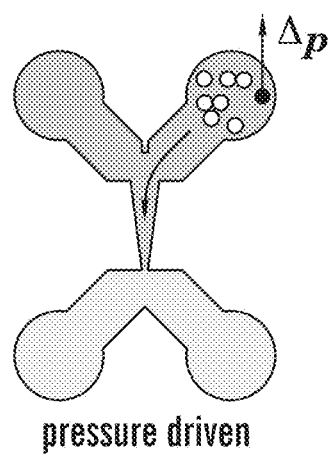
FIGS. 6A-6E show examples of a process for bacteria capture/immobilization in the microchannel.
Figure 6B:
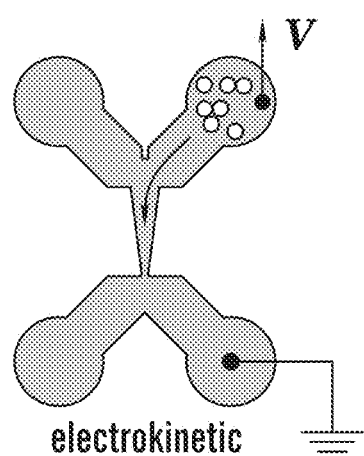
Figure 6C:
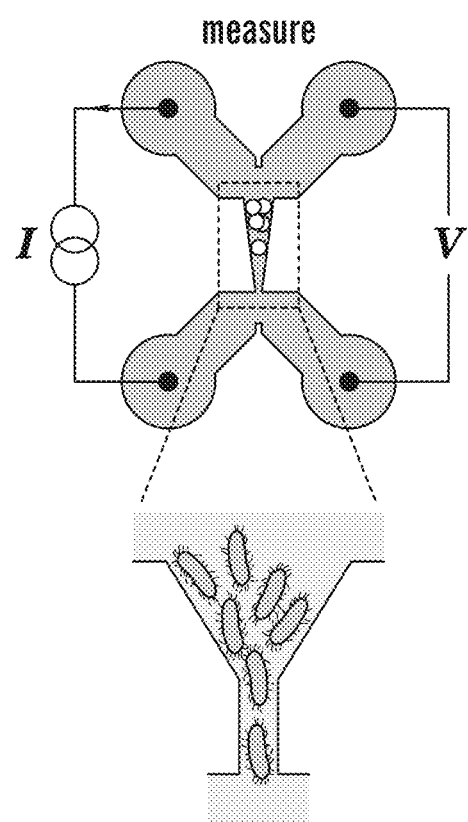

FIGS. 6A-6D show a process for the capture and/or immobilization of bacteria in the microchannel 120 according to some embodiments of the invention. The bacteria solution (e.g., urine) can be pushed through the microchannel by establishing either a pressure-driven flow or an electrokinetic flow. Motile bacteria (e.g., E. coli) can be immobilized by specific and non-specific surface chemistry;

or by using a high flow force causing the bacteria cells to jam into the tight microchannel. Non-motile bacteria settle and stick to the microchannel typically on their own. After the capture/immobilization, the bacteria do not leave the microchannel but continue their nanomechanical movements. In accordance with some embodiments of the invention, capturing and immobilizing the bacteria allows for monitoring the viability of a small population of cells as shown in FIG. 6C.

Figure 6D:
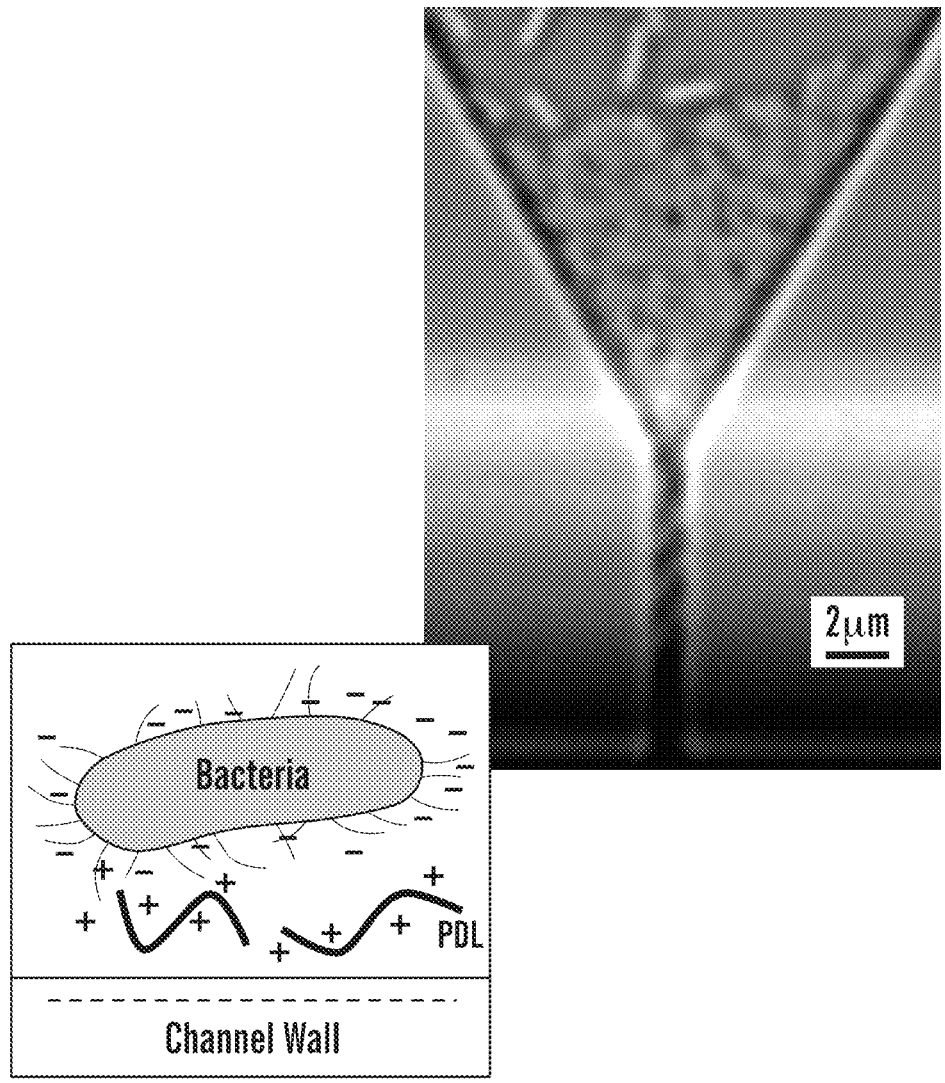
Figure 6E:
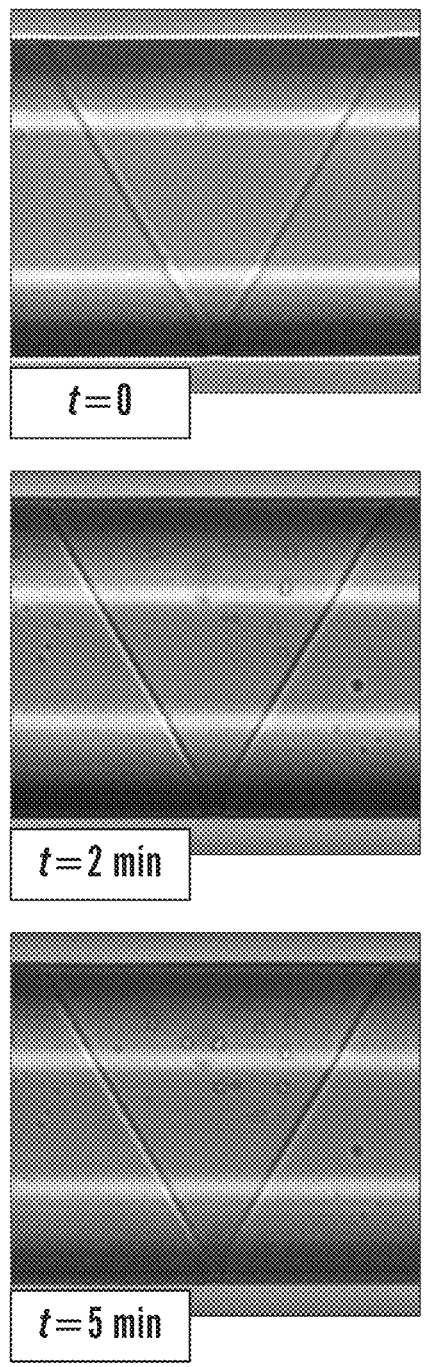

FIG. 6D shows *E. coli* immobilized in a microchannel by flow. The microchannel tapers from a width of 30 µm down to 1 µm; the entire taper region in FIG. 6D has a height of about 1 µm. The third dimension (i.e., the microchannel height) is useful for the capture and the measurements. The measured electrical signals correspond to bacterial movements in the entire taper region. To increase the capture efficiency, the microchannel surface can be coated with an adhesion promoting layer, such as Poly-D-Lysine (PDL), which is a positively charged amino acid (FIG. 6D inset). Shortly after the flow was established, cells accumulated in the taper and adhered to the surface. During this step, the mean (dc) electrical resistance was monitored and was used to determine how many bacteria were immobilized in the taper region (i.e., microscope is not needed). There are about 50 cells in FIG. 6D, including those in the constriction, all of which contribute to the electrical fluctuations that were measured. A selective layer such as a coating including an antibody can also be applied to the microchannel surface to capture the bacteria selectively.

An advantage of this approach is that it can increase the effective local density of bacteria in the microchannel region by orders of magnitude in a time frame of 10s of minutes. For example, see FIG. 6E, which shows a sample with a concentration of about $10^5$ CFU/ml that was pipetted into the device (FIG. 6A), creating a pressure-driven flow. The flow carries the non-motile cells (*S. epidermidis*) into the microchannel region steadily and deposits them there. The images taken at t=0, 2 min. and 5 min. show that a significant density increase can be achieved in a relatively short time.

Figure 7A:
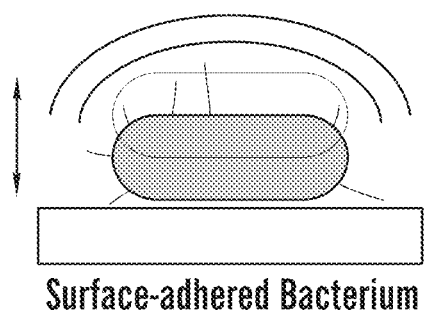
FIGS. 7A and 7B are schematics of embodiments where bacteria can be adhered or otherwise attached to the surface of the walls of the microchannel and can be modeled as a bacteria attached to the wall by a spring.
Figure 7B:
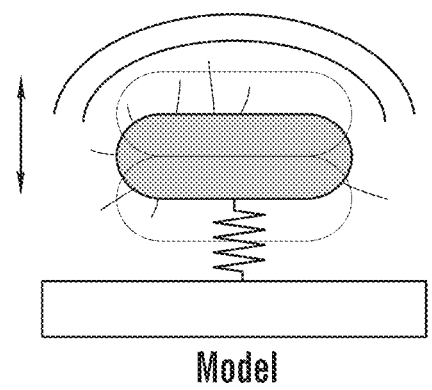

As previously stated, motile bacteria generate electrical fluctuations by swimming into and out of the microchannel region. Similarly, live bacteria adhered to a surface demonstrate similar electrical fluctuations and can be measured and detected using electrical signals in a microchannel or microchannel in accordance with the principals of the present invention. Thus, present invention can be used to detect and monitor bacteria bound to a substrate as well as planktonic bacteria in a channel. FIG. 7A shows a bacterium adhered onto a surface exhibiting nanomechanical fluctuations. As shown in FIG. 7B, the chemical or physical bond between the bacterium and the surface can be modeled as a spring wherein the bacterium exerts a steady but random force on the spring, resulting in large amplitude (10s of nm) random vibrations.

Figure 8A:
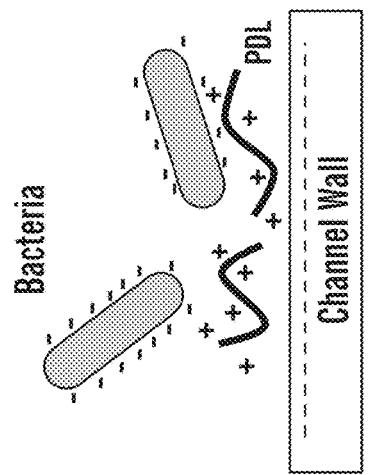
FIGS. 8A and 8B show a system according to some embodiments of the invention where non-motile bacteria can be detected and monitored to test for antibiotic susceptibility.
Figure 8B:
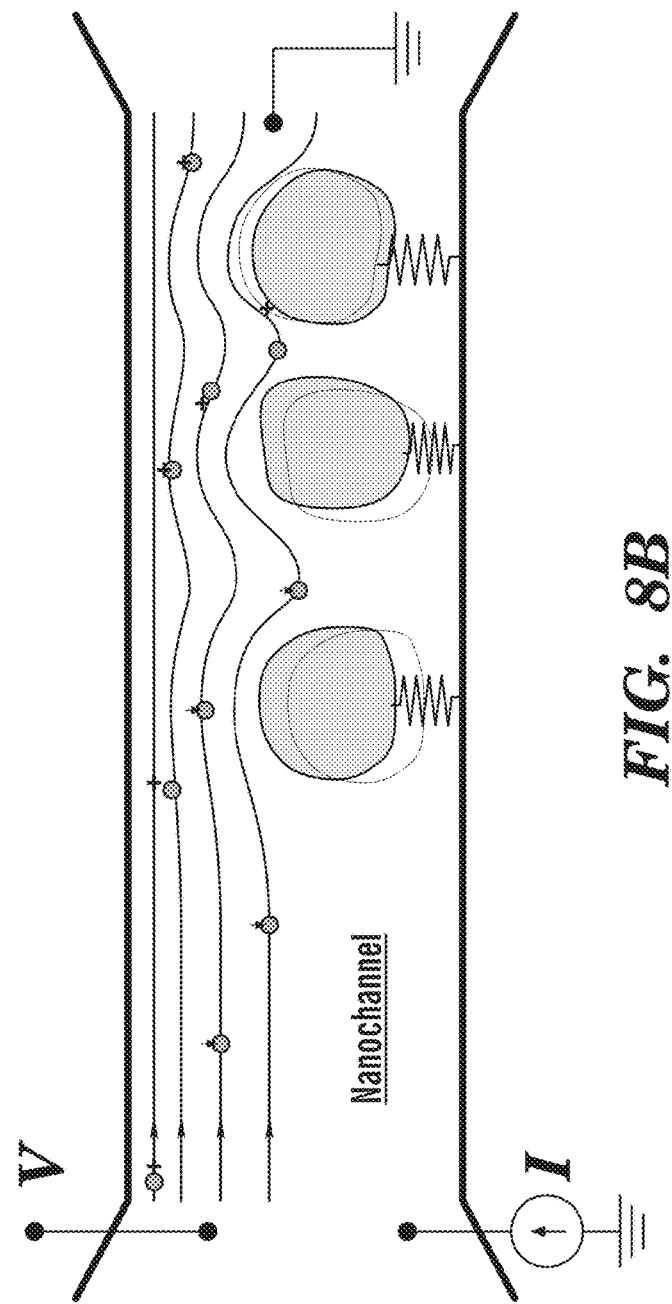

FIGS. 8A and 8B show a system according to some embodiments of the invention wherein non-motile bacteria can be detected and monitored to test for antibiotic susceptibility. In accordance with some embodiments of the invention, non-motile bacteria (e.g., *S. epidermidis*) can be adhered onto the surfaces of a microchannel. The nanomechanical fluctuations of the bacteria on the surface will randomly modulate the microchannel diameter, thereby resulting in detectable electrical signal fluctuations. In other words, the nanomechanical fluctuations of the bacteria adhered on the channel walls will produce the electrical (voltage) fluctuations indicative of the presence of live bacteria in the channel. Upon administering antibiotics, the bacterial activity will stop and the electrical fluctuations will subside.

FIG. 8A shows an electrostatic interaction can be formed between the channel wall, and *E. coli* to adhere the bacteria on the microchannel walls. The microchannel acquires a negative surface charge when hydrated. In contrast, the bacteria have negatively charged cell walls. Therefore, by subsequently coating the channel surfaces with Poly-D-Lysine (PDL), which is a positively charged amino acid, by flowing a PDL solution through the microchannel, the bacteria can be caused to adhere easily to the PDL coating via electrostatic forces. FIG. 8B shows the nanomechanical models of the microchannel walls with adhered bacteria, exemplifying the springs model the PDL and are electrostatic in nature. This process can be used to adhere different types of bacteria onto the microchannel walls. The electrical signal fluctuation measurement can be used to detect whether the bacteria are dead or alive.

Figure 9A:
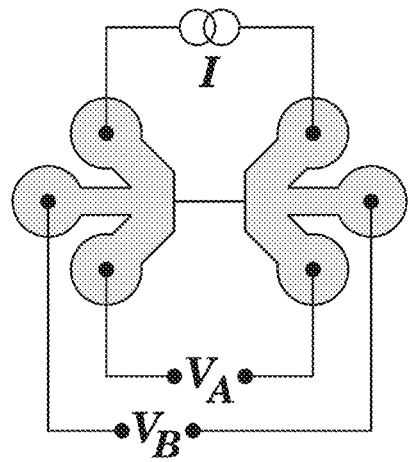
FIGS. 9A-9C shows implementation of different measurement systems.

FIG. 9A shows a system according to some embodiments of the invention, where correlation measurement can be implemented. In accordance with some embodiments of the invention, a second pair B of electrodes ($V_B$) can be inserted but through separate paths as shown in FIG. 9A. The current can be applied as before through one electrode pair. Then, the voltage ($V_A$) fluctuations measured through electrode pair A can be cross-correlated with those measured through B: $<V_A(t)V_B(t)>$. In this embodiment, a more sensitive measurement of the fluctuations can be obtained. Furthermore, the fluctuations not coming from the microchannel region (i.e., the bacteria) can be reduced and/or eliminated.

Figure 9B:
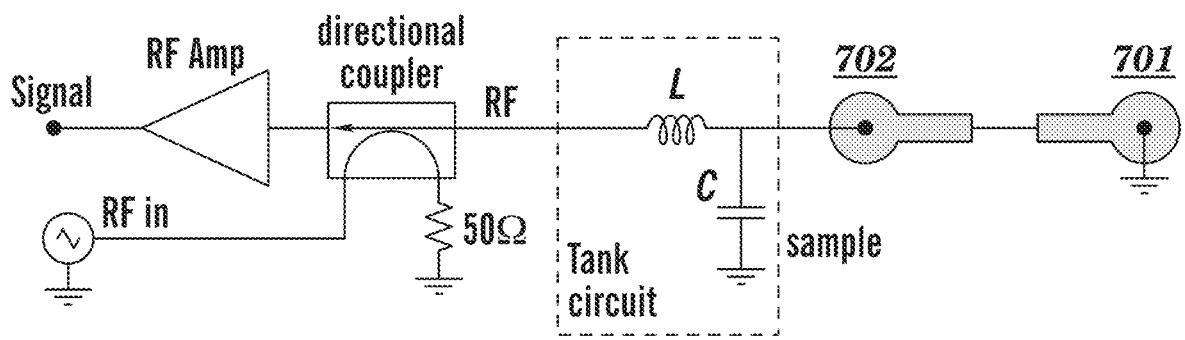
Figure 9C:
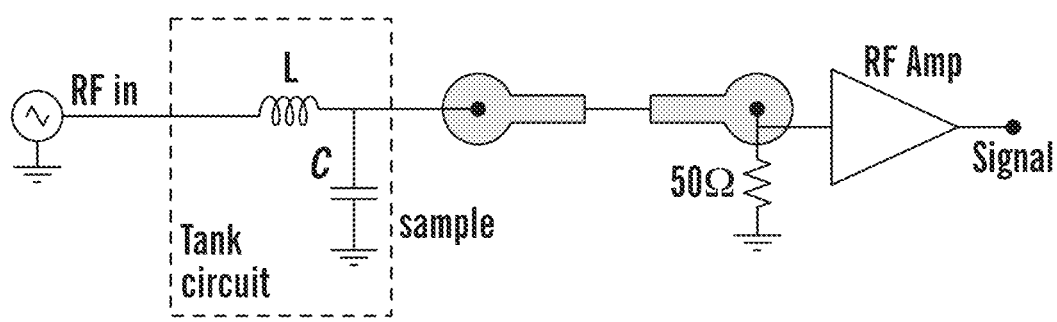

FIG. 9B shows a system according to some embodiments of the invention, where radiofrequency (RF) signal techniques can be implemented. In accordance with some embodiments of the invention, a low-noise RF amplifier can be used obtain more precise signal measurements. In addition, the RF measurements can provide much larger bandwidths and/or much smaller time resolution (e.g., latency). Furthermore, in these embodiments, applying a direct current through the microchannel may not be necessary. As shown in FIG. 9B, a basic RF reflectometry measurement circuit is provided wherein RF signal waves are reflected from the electrodes (701, 702) across the microchannel. Electrode 701 can be grounded and the other electrode 702 can be connected to the reflectometer. This measurement provides the complex impedance, Z(t), of the microchannel as a function of time. The imaginary part of the impedance may change more strongly than the real part (i.e., resistance), making this measurement useful for bacteria as well as other particles. In accordance with some embodiments of the invention, the system can include the RF transmission measurement shown in FIG. 9C. In both embodiments, an impedance matching circuit can be used (i.e., an LC tank circuit) to better couple the power to the microchannel region of the circuit.

Figure 10:
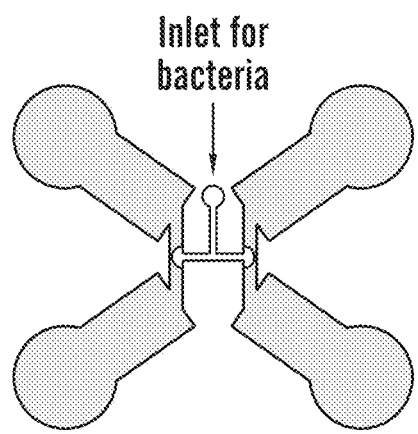
FIG. 10 shows an alternative antibiotic susceptibility testing system where there exists a significant reduction of sample volume in accordance with some embodiments of the invention.

FIG. 10 shows an antibiotic susceptibility testing system according to some embodiments of the invention that is adapted to accommodate very small sample volumes. In accordance with some embodiments of the invention, the bacteria can be confined to the microchannel by using microfabricated structures on the channel walls. In accordance with some embodiments of the invention, the relevant sample volume can be approximately the volume of the microchannel, which is be preconfigured to accommodate very small sample volumes. FIG. 10 shows an antibiotic susceptibility testing system, which uses an extremely small sample volume. Here, the bacteria are only introduced into the microchannel regions of the system through a separate inlet. Microfabricated meshes or pillars can be used to separate the microchannel region from the mm-sized reservoirs. These meshes can be used restrict bacteria to the microchannel regions. The ions in the solution can move through the meshes without being hindered. Because the signal (i.e., fluctuations of bacteria) is coupled to the motion of electrical ions and not the bulk fluid flow, the sensitivity in the device is not degraded. In accordance with some embodiments of the invention, testing system using these microfabricated meshes and/or pillars can be used to test very small bacteria volumes (e.g., tens of bacteria). In accordance with some embodiments of the invention, non-motile bacteria can also be tested by adhering the non-motile bacteria to the microchannel surfaces using favorable surface chemistry. These embodiments can be used to test small sample volumes on the order of 10-100 picoliters ($10^{-8}$-$10^{-7}$ ml).

Figure 11:
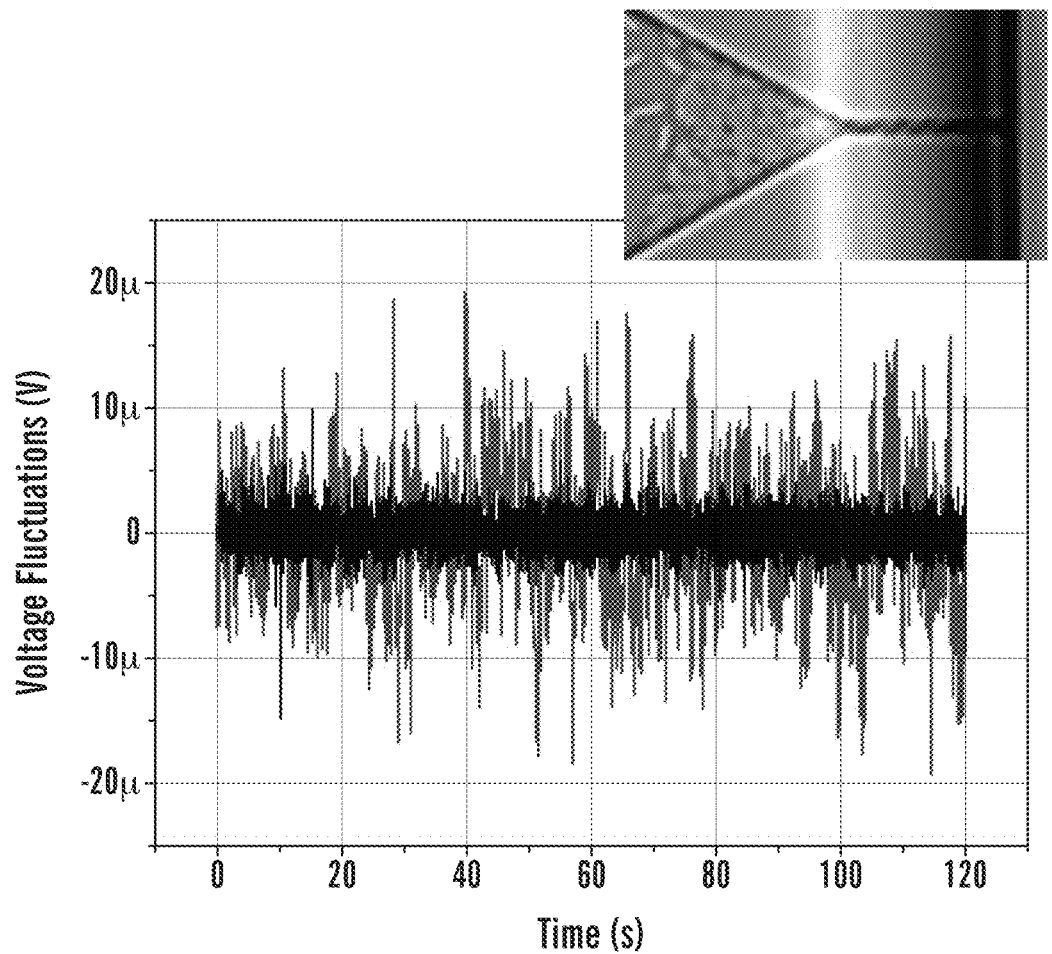
FIG. 11 shows the detection of movements of surface immobilized motile bacteria, *E. coli.* wherein the red trace shows the time-dependent electrical fluctuations due to nanomechanical movements of about 50 cells.

In accordance with some embodiments of the invention, after capture, the viability of bacteria can be detected from their movements. FIG. 11 shows a measured electrical signal (red trace) from about 50 *E. coli* along with the background (black trace). These cells are shown in the inset of FIG. 11. Once the bacteria cells are jammed or adhered to the microchannel surface, they do not leave the microchannel region, but continue their random nanomechanical oscillations in place that give rise to the observed electrical fluctuations. The root-mean square (RMS) values with and without bacteria are 1.68 µV and 6.31 µV, respectively.

Non-motile bacteria on a surface move incessantly by going through subtle random oscillations (wiggles). These movements were first detected by means of a microcantilever, see Nanomechanical motion of *Escherichia coli* adhered to a surface, C Lissandrello, F Inci, M Francom, M R Paul, U Demirci, K L Ekinci, Applied physics letters 105 (11), 113701, which is hereby incorporated by reference in its entirety.

Figure 12B:
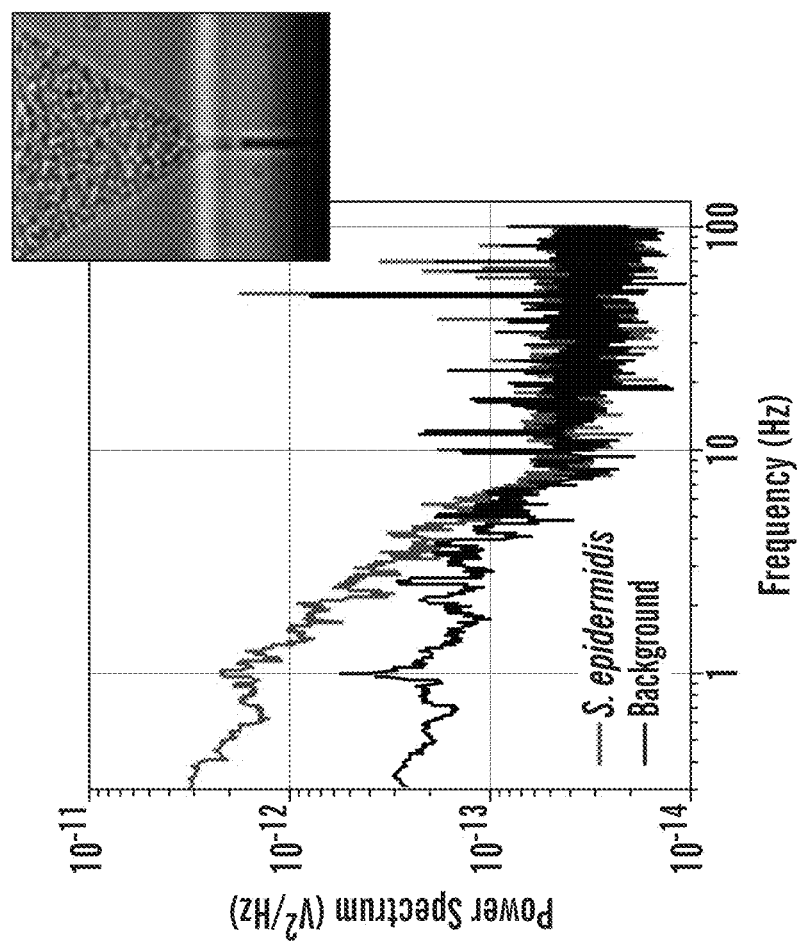
FIGS. 12A and 12B show the electrical fluctuations caused by movements of non-motile bacteria, *S. epidermidis*.
Figure 12A:
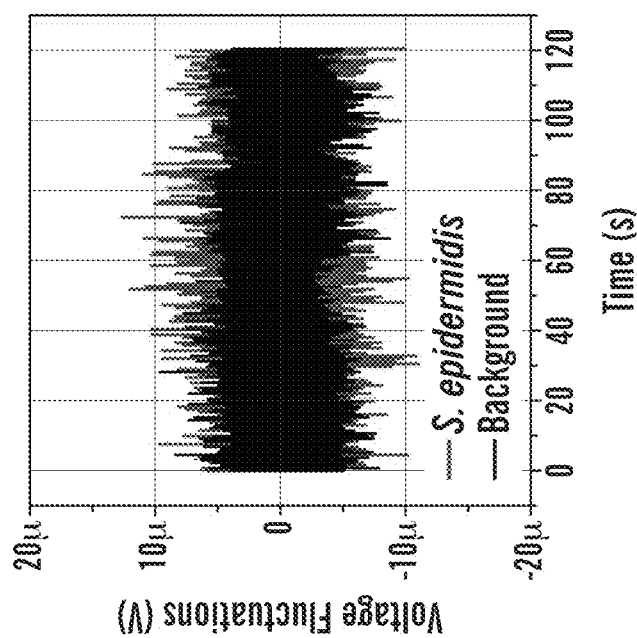

The data in FIG. 12A shows that these subtle movements of non-motile bacteria are detectable using a nanochannel or microchannel transducer in accordance with the invention. Experiments were performed with *S. epidermidis*, which is a non-motile bacteria very similar to *S. aureus* but less virulent. The cells were adhered to the microchannel walls from solution as above in FIGS. 6A-6E. The microscope image in the inset of FIG. 12B shows that the cells completely fill the tapered microchannel and top half of the tight constriction. The electrolyte filling the device is a nutrient broth. FIG. 12A shows two electrical voltage signal traces as a function of time—the background signal (black) and the fluctuation signal with *S. epidermidis* in the microchannel (red). A slight increase can be observed in the fluctuations. A frequency-domain analysis provides more insight and makes the subtle features in the data prominent. FIG. 12B shows the power spectra of the fluctuations, obtained numerically from the time-domain signals in FIG. 12A. The figures show that the fluctuations have increased significantly at frequencies in the range 0.3 Hz<f<10 Hz.

Example

FIGS. 13A, 13B, and 13C show the results of antibiotic susceptibility studies in human urine. In this example, two strains of *E. coli* are used, with one being resistant to the administered antibiotic, nalidixic acid. The two strains are immobilized in two separate but identical chips, such as shown in FIG. 6D. The electrolyte filling the chips is a urine/broth/antibiotic mixture, with the antibiotic concentration set above the minimum inhibitory concentration (MIC) level. The voltage fluctuations of about 50 bacteria are shown in FIGS. 13A and 13B, as a function of time, after the antibiotic is administered. The x-axes in FIGS. 13A and 13B show real time. The voltage fluctuations of the resistant strain do not show significant changes over time, as determined from the root-mean square (RMS) amplitude of the voltage fluctuations. The voltage fluctuations for the susceptible strain are seen to decay rather quickly. FIG. 13C shows the RMS values of the fluctuations in a bar graph as a function of time for both the resistant and the susceptible strains. This measurement suggests that, in accordance with some embodiments of the invention, the time for a conclusive test should be approximately 2 hours.

For these experiments, commercially-acquired urine (BioreclamationIVT, Long Island, N.Y.) with the following properties was used: pH=6; resistivity≈10 mS/cm (excellent conductor); with some large crystals (>10 µm). After spiking with bacteria and mixing with broth/antibiotics, the urine was filtered in a large-pore-size filter. The filtered urine was then directly pipetted into the device as the test matrix. The final bacteria concentration was about $10^5$-$10^6$ CFU/ml, close to clinical concentrations in UTI.

Figure 14:
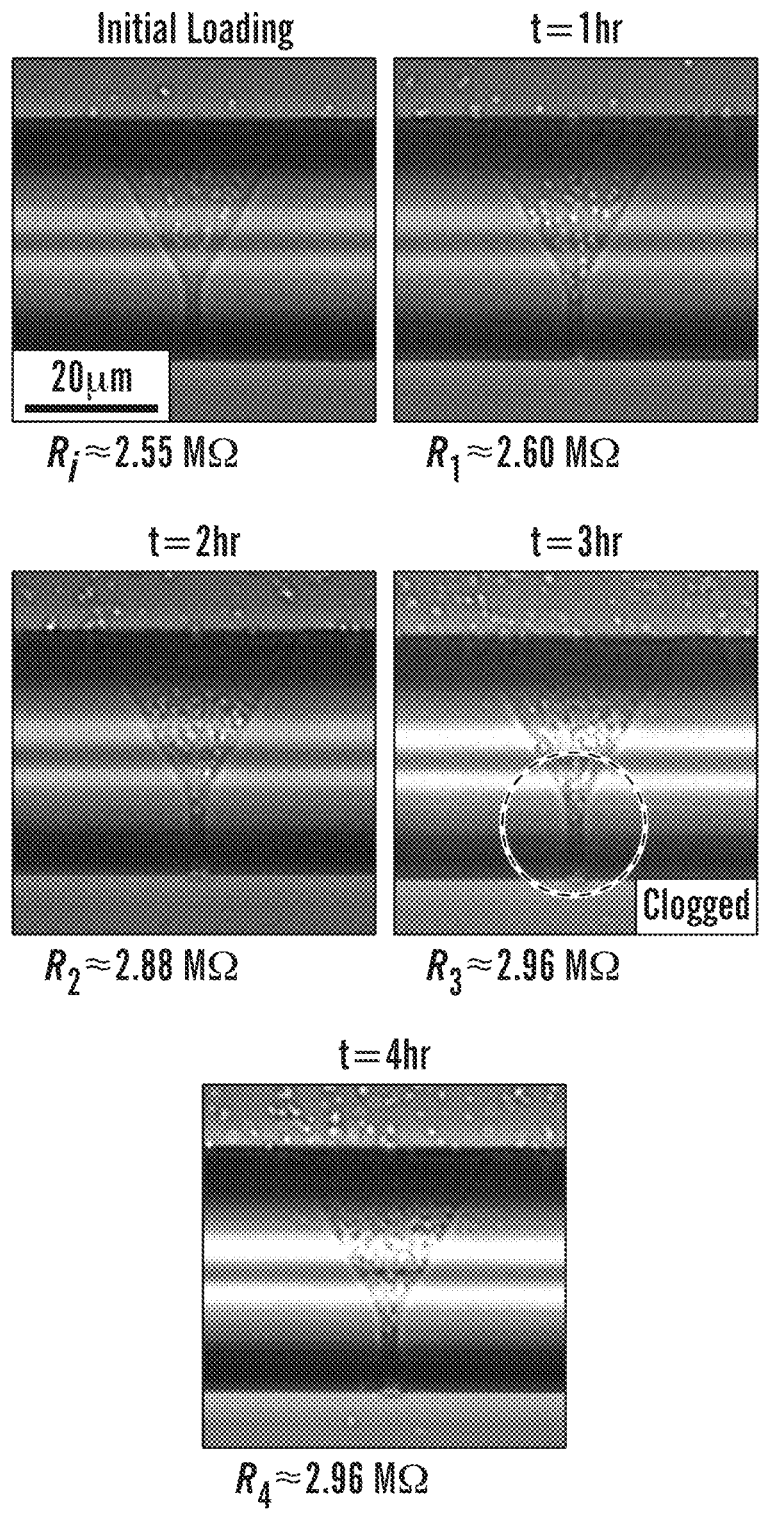
FIG. 14 shows microscope images of the microchannel filled with only the Bacteria (*S. epidermidis*) at t=0, 1 hr., 2 hrs., 3 hrs. and 4 hrs.
Figure 15:
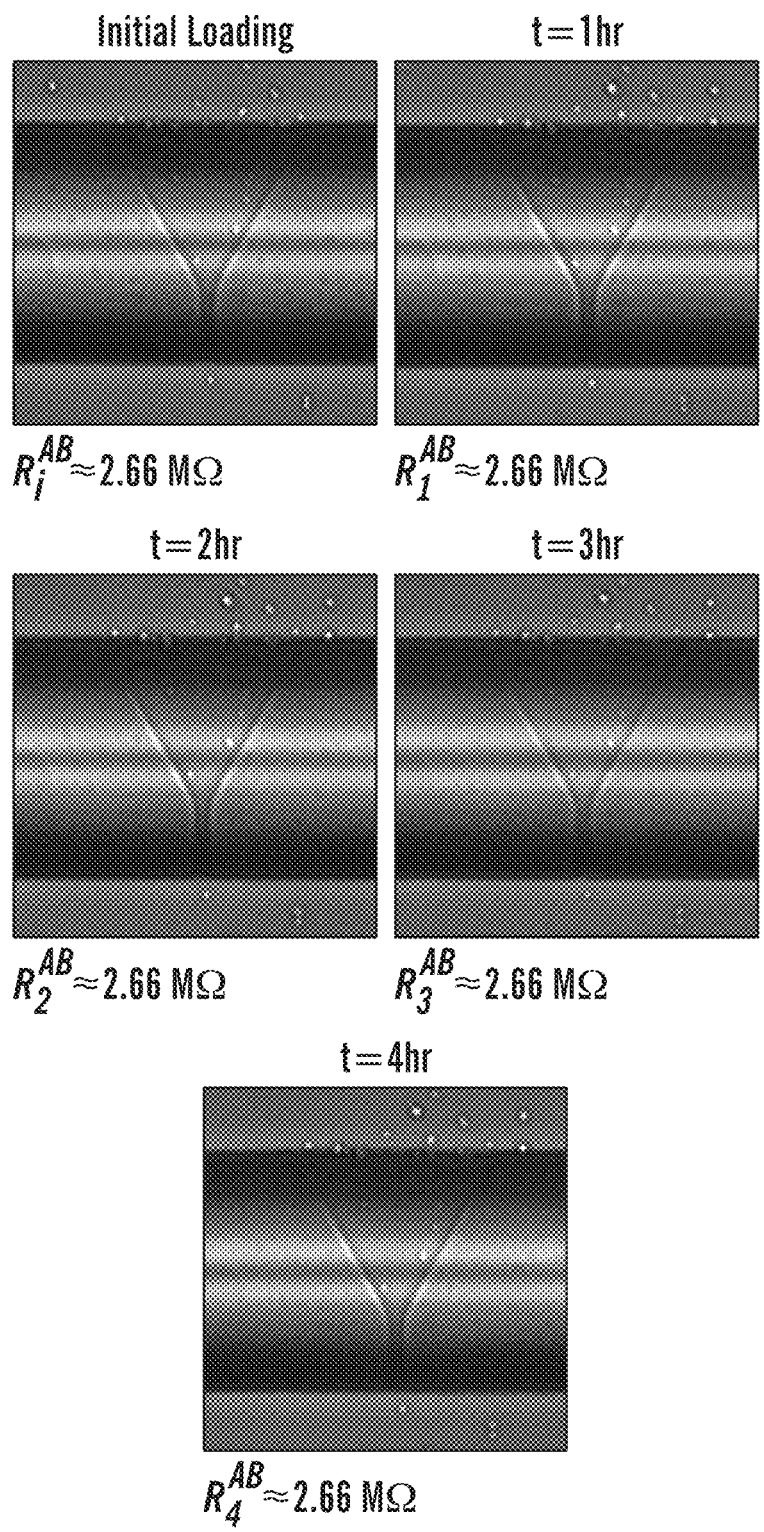
FIG. 15 shows microscope images of the microchannel filled with the Bacteria (*S. epidermidis*) and an effective antibiotic vancomycin 4 µg/ml at t=0, 1 hr., 2 hrs., 3 hrs. and 4 hrs.
Figure 16:
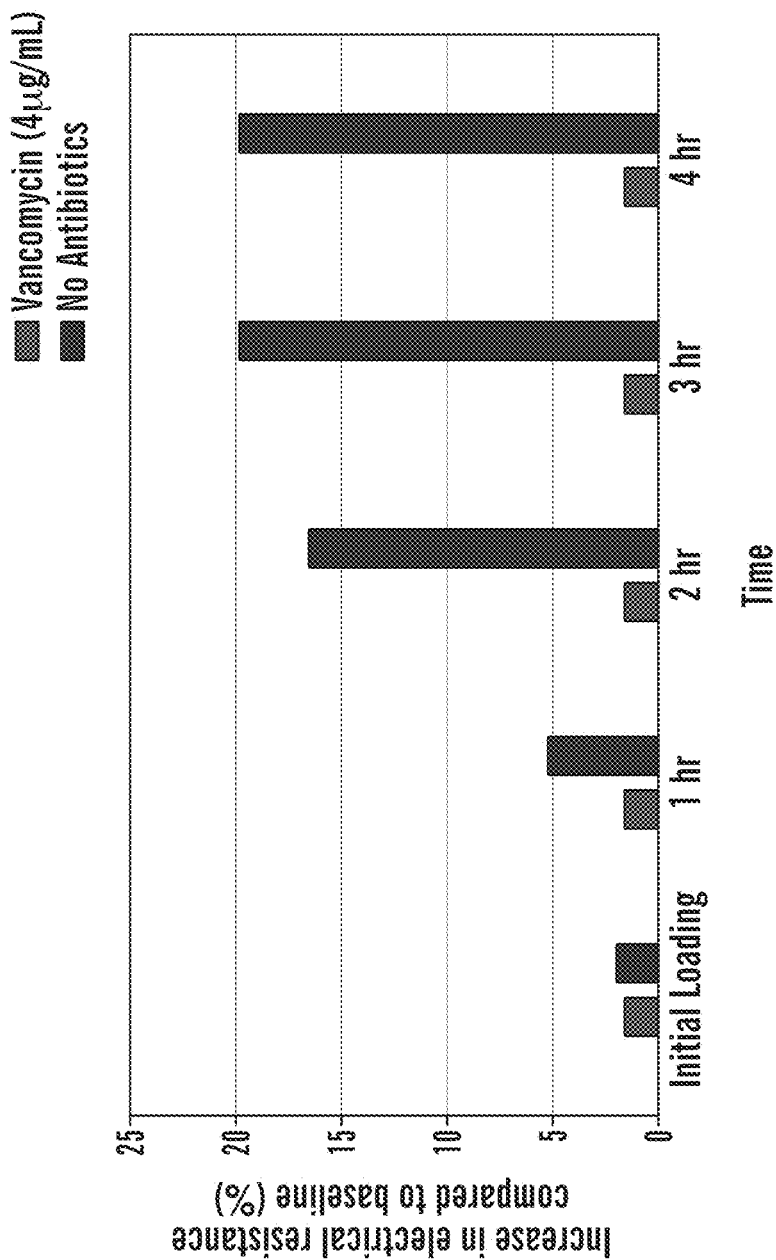
FIG. 16 shows a bar chart of the change in mean resistance that reflects the size of the bacteria population in broth (no antibiotics) and in antibiotics/broth solutions at t=0, 1 hr., 2 hrs., 3 hrs. and 4 hrs. The microscope images shown in FIGS. 14 and 15 are snapshots of the bacteria with no antibiotics and in the presence of antibiotics, respectively, measured in FIG. 16 and show how the technique works. The resistance changes shown in FIG. 16 are given with respect to the empty microchannel resistance.

In the experiment shown in FIGS. 14, 15 and 16, the susceptibility of *S. epidermidis* to Vancomycin was tested using the mean resistance based approach shown in the flowchart in FIG. 4. As discussed above, *S. epidermidis* is non-motile and readily settles in the microchannel. Two identical chips were prepared, one filled with broth solution as shown in FIG. 14 (and represented by the blue data bars on the right in FIG. 16) and the other with broth/Vancomycin mixture as shown in FIG. 15 (and represented by the green data bars on the left in FIG. 16). The changes in the mean resistances, which reflect the sizes of the *S. epidermidis* populations, are shown as a function of time in the bar graphs of FIG. 16. As discussed above, the population in broth continues to grow until the microchannel is completely filled. On the other hand, in the antibiotic solution, the population size stays the same (microscope images not shown). This is accurately reflected in the mean resistance value, which does not change noticeably. In accordance with some embodiments of the invention, the antibiotic susceptibility can be determined in a time scale comparable to the cell division time.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Although any known methods, devices, and materials may be used in the practice or testing of the invention, the methods, devices, and materials in this regard are described herein.

Definitions

Unless stated otherwise, or implicit from context, the following terms and phrases include the meaning provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention. Further, unless otherwise required by context, singular terms shall include plural and plural terms shall include the singular.

As used herein, the term "comprising" or "comprises" is used in reference to compositions, methods, and respective component(s) thereof, that are useful to an embodiment, yet open to the inclusion of unspecified elements, whether useful or not.

As used herein, the term "consisting essentially of" refers to those elements for a given embodiment. The term permits the presence of elements that do not materially affect the basic and novel or functional characteristic(s) of that embodiment of the invention.

Other than in the operating examples, or where otherwise indicated, all numbers expressing quantities of ingredients or reaction conditions used herein should be understood as modified in all instances by the term "about." The term "about" when used in connection with percentages may mean±1% of the value being referred to. For example, about 100 means from 99 to 101.

The abbreviation, "e.g." is derived from the Latin exempli gratia, and is used herein to indicate a non-limiting example. Thus, the abbreviation "e.g." is synonymous with the term "for example."

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

What is claimed is:

1. A method for detecting live bacteria in a microchannel comprising:
    a) providing a constant current or constant voltage through a microchannel wherein the microchannel does not contain any bacteria and measuring baseline resistance through the microchannel to determine a baseline resistance fluctuation signal;
    b) providing a constant current or constant voltage through a microchannel wherein the microchannel contains at least one bacterium and measuring resistance fluctuations through the microchannel to determine a first resistance fluctuation signal; and
    c) determining that the at least one bacterium is alive if the first resistance fluctuation signal is greater than the baseline resistance fluctuation signal by a predefined threshold amount.

2. The method according to claim 1 wherein the baseline resistance fluctuation signal is determined as a function of the measured baseline resistance fluctuations and the first resistance fluctuation signal is determined as a function of the measured resistance fluctuations.

3. The method according to claim 2 wherein the baseline resistance fluctuation signal includes an RMS signal level determined as a function of the measured baseline resistance fluctuations and the first resistance fluctuation signal includes an RMS signal level determined as a function of the measured resistance fluctuations.

4. The method according to claim 1 further comprising:
    (d) adding an antibiotic to the microchannel;
    (e) providing a constant current or constant voltage through the microchannel wherein the microchannel contains the at least one bacterium and the antibiotic, and measuring resistance fluctuations through the microchannel to determine a second voltage or current fluctuation signal; and
    (f) determining that the at least one bacterium is susceptible to the antibiotic if the second resistance fluctuation signal falls within a predefined threshold amount of the baseline resistance fluctuation signal after a predetermined period of time.

5. The method according to claim 4 wherein:
    the baseline resistance fluctuation signal includes an RMS signal level determined as a function of the measured baseline voltage or current fluctuations;
    the first resistance fluctuation signal includes an RMS signal level determined as a function of the measured resistance fluctuations; and
    the second resistance fluctuation signal includes an RMS signal level determined as a function of the measured resistance fluctuations.

6. The method according to claim 4 wherein the at least one bacterium is determined to be susceptible to the antibiotic if the second resistance fluctuation signal falls within ten percent of the baseline resistance fluctuation signal after a predetermined period of time.

* * * * *